(12) United States Patent
Evans et al.

(10) Patent No.: US 12,053,776 B2
(45) Date of Patent: *Aug. 6, 2024

(54) FLOWCELLS WITH LINEAR WAVEGUIDES

(71) Applicants: ILLUMINA CAMBRIDGE LIMITED, Cambridge (GB); ILLUMINA, INC., San Diego, CA (US)

(72) Inventors: Geraint Evans, Cambridge (GB); Stanley S. Hong, Menlo Park, CA (US)

(73) Assignees: ILLUMINA CAMBRIDGE LIMITED, Cambridge (GB); ILLUMINA, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/854,741

(22) Filed: Jun. 30, 2022

(65) Prior Publication Data
US 2022/0331798 A1 Oct. 20, 2022

Related U.S. Application Data

(63) Continuation of application No. 17/255,765, filed as application No. PCT/US2020/070063 on May 19, 2020, now Pat. No. 11,406,977.
(Continued)

(51) Int. Cl.
*G01N 21/05* (2006.01)
*B01L 3/00* (2006.01)
(Continued)

(52) U.S. Cl.
CPC ........ B01L 3/502715 (2013.01); G01N 21/05 (2013.01); G02B 27/4227 (2013.01);
(Continued)

(58) Field of Classification Search
CPC .......... G01N 21/05; G01N 2021/6482; G02B 27/4227; B01L 3/502715;
(Continued)

(56) References Cited

U.S. PATENT DOCUMENTS 6,078,705 A   6/2000  Neuschafer et al.
6,483,096 B1  11/2002 Kunz et al.
(Continued)

FOREIGN PATENT DOCUMENTS

CN    104538841 A    4/2015
CN    106796175 A    5/2017
(Continued)

OTHER PUBLICATIONS

International Search Report and Written Opinion received for PCT/US2020/070063, dated Aug. 25, 2020.
(Continued)

*Primary Examiner* — Brian J. Sines
(74) *Attorney, Agent, or Firm* — MARSHALL, GERSTEIN & BORUN LLP

(57) ABSTRACT

For example, a flowcell includes: a nanowell layer having a first set of nanowells and a second set of nanowells to receive a sample; a first linear waveguide associated with the first set of nanowells, and a second linear waveguide associated with the second set of nanowells; and a first grating for the first linear waveguide, and a second grating for the second linear waveguide, the first and second gratings providing differential coupling of first light and second light.

15 Claims, 16 Drawing Sheets

Related U.S. Application Data

(60) Provisional application No. 62/868,423, filed on Jun. 28, 2019.

(51) Int. Cl.
*C12Q 1/6869* (2018.01)
*G01N 21/64* (2006.01)
*G02B 27/42* (2006.01)

(52) U.S. Cl.
CPC .......... *B01L 2300/0829* (2013.01); *B01L 2300/0861* (2013.01); *B01L 2300/0896* (2013.01); *C12Q 1/6869* (2013.01); *G01N 2021/6482* (2013.01)

(58) Field of Classification Search
CPC ..... B01L 2300/0829; B01L 2300/0861; B01L 2300/0896; C12Q 1/6869
See application file for complete search history.

(56) References Cited

U.S. PATENT DOCUMENTS

| | | |
|---|---|---|
| 7,476,503 B2 | 1/2009 | Turner et al. |
| 11,406,977 B2 * | 8/2022 | Evans ............... G02B 27/4227 |
| 2003/0012483 A1 | 1/2003 | Ticknor et al. |
| 2003/0027328 A1 | 2/2003 | Cunningham et al. |
| 2005/0110989 A1 | 5/2005 | Schermer et al. |
| 2006/0008206 A1 | 1/2006 | Maisenhoelder et al. |
| 2007/0009968 A1 | 1/2007 | Cunningham et al. |
| 2008/0128627 A1 | 6/2008 | Lundquist et al. |
| 2009/0247414 A1 | 10/2009 | Obradovic et al. |
| 2011/0306143 A1 | 12/2011 | Chiou et al. |
| 2013/0288357 A1 | 10/2013 | Tiefenthaler |
| 2014/0178861 A1 | 6/2014 | Duer |
| 2016/0216538 A1 | 7/2016 | McDonald et al. |
| 2017/0016827 A1 | 1/2017 | Gervais et al. |
| 2018/0172906 A1 | 6/2018 | Rothberg et al. |

FOREIGN PATENT DOCUMENTS

| | | |
|---|---|---|
| JP | 2003-527580 A | 9/2003 |
| JP | 2005-338098 A | 12/2005 |
| JP | 2013-524174 A | 6/2013 |
| JP | 2017-512306 A | 5/2017 |
| JP | 2019-049530 A | 3/2019 |
| RU | 2422204 C2 | 6/2011 |
| WO | WO-01/43875 A1 | 6/2001 |
| WO | WO-2008/028160 A2 | 3/2008 |
| WO | WO-2015/111458 A1 | 7/2015 |
| WO | WO-2018/013243 A1 | 1/2018 |

OTHER PUBLICATIONS

International Search Report and Written Opinion received for PCT/IB2020/055055, dated Aug. 17, 2020.

Kehagias et al.: "Stamp replication for thermal and UV nanoimprint lithography using a UV-sensitive silsesquioxane resist", Microelectronic Engineering, vol. 86, 2009, pp. 776-778, XP026106271.

Search Report received for NL Application No. 2023516, dated Jul. 17, 2019.

* cited by examiner

FLOWCELLS WITH LINEAR WAVEGUIDES

CROSS-REFERENCE TO RELATED APPLICATIONS

This application a continuation application of U.S. patent application Ser. No. 17/255,765, filed Dec. 23, 2022, which is a 35 U.S.C. § 371 National Stage of International Patent Application No. PCT/US2020/070063, filed May 19, 2020, which itself claims the benefit of and priority to U.S. Provisional Patent Application No. 62/868,423, filed on Jun. 28, 2019, the content of each of which is incorporated by reference herein in its entirety and for all purposes.

BACKGROUND

Samples of different materials can be analyzed using one or more of a variety of analytical processes. For example, sequencing such as high-throughput DNA sequencing can be the basis for genomic analysis and other genetic research. For example, sequencing by synthesis (SBS) technology uses modified deoxyribonucleotide triphosphates (dNTPs) including a terminator and a fluorescent dye having an emission spectrum. In this and other types of sequencing, characteristics of a sample of genetic material are determined by illuminating the sample, and by detecting emission light (e.g., fluorescent light) that is generated in response to the illumination.

It may be desirable to ensure good quality of the analysis of the sample as well as to facilitate that the analysis is performed at relatively high speed. For example, the amount of the sample material that is analyzed at each individual stage drives the resulting throughput of the analysis process. It may be attempted to distribute the sample material more densely in the analysis equipment to allow more material to be analyzed at any given time. However, characteristics of the analysis system such as the maximum resolution available from imaging optics may limit the extent to which such an approach can increase the throughput.

SUMMARY

In a first aspect, a flowcell includes: a nanowell layer having a first set of nanowells and a second set of nanowells to receive a sample; a first linear waveguide associated with the first set of nanowells, and a second linear waveguide associated with the second set of nanowells; and a first grating for the first linear waveguide, and a second grating for the second linear waveguide, the first and second gratings providing differential coupling of first light and second light.

Implementations can include any or all of the following features. The first and second gratings are spatially offset from each other. The first and second linear waveguides are positioned adjacent to each other, the flowcell further comprising: a third linear waveguide positioned adjacent to the second linear waveguide opposite from the first linear waveguide. The third linear waveguide shares the first grating with the first linear waveguide. The flowcell further comprises a third grating for the third linear waveguide. The third grating has the same spatial offset from the second grating as has the first grating. The third grating is spatially offset from each of the first and second gratings. The first grating is positioned toward a first end of the first linear waveguide, wherein the second grating is positioned toward a second end of the second linear waveguide, and wherein the first end is positioned opposite from the second end. The first grating is positioned on a triangular substrate. The first and second gratings have different grating periods from each other. The first and second linear waveguides are positioned adjacent each other, the flowcell further comprising: a third linear waveguide positioned adjacent to the second linear waveguide opposite from the first linear waveguide; and a third grating for the third linear waveguide. The third grating has the same grating period as the first grating. The third grating has a grating period different from each of the grating periods of the first and second gratings. The nanowells in at least one of the first and second sets of nanowells have a spacing from each other that is resolvable according to a resolution distance of emission optics for the flowcell. The first and second linear waveguides are positioned closer to each other than the resolution distance of the emission optics. The differential coupling of the first light comprises coupling the first light into the first linear waveguide and minimizing coupling of the first light into the second linear waveguide. The differential coupling of the second light comprises coupling the second light into the second linear waveguide and minimizing coupling of the second light into the first linear waveguide. The differential coupling is at least in part due to a coupler parameter of one or more of the first grating or the second grating. The coupler parameter comprises at least one selected from the group consisting of: a refractive index, a pitch, a groove width, a groove height, a groove spacing, a grating non-uniformity, a groove orientation, a groove curvature, a coupler shape, and combinations thereof. The differential coupling is at least in part due to a waveguide parameter of one or more of the first linear waveguide or the second linear waveguide. The waveguide parameter comprises at least one selected from the group consisting of: a cross sectional profile, a refractive index difference, a mode matching, and combinations thereof. The first and second sets of nanowells are arranged in a polygonal array. The polygonal array comprises a rectangular array or a hexagonal array. The first and second sets of nanowells are arranged in the hexagonal array, which forms at least one hexagon, the hexagon including: first and second nanowells of the first set of nanowells, the first and second nanowells being part of a first row of nanowells that extends along the first linear waveguide; third, fourth and fifth nanowells of the second set of nanowells, the third, fourth and fifth nanowells being part of a second row of nanowells that extends along the second linear waveguide; and sixth and seventh nanowells of a third set of nanowells, the sixth and seventh nanowells being part of a third row of nanowells that extends along a third linear waveguide. The first set of nanowells comprises a first row of nanowells, and wherein the second set of nanowells comprises a second row of nanowells. Each of the first and second rows of nanowells is aligned with at least one of the first and second linear waveguides. The first row of nanowells extends along the first linear waveguide, wherein the second row of nanowells extends along the second linear waveguide, wherein the first linear waveguide is parallel and adjacent to the second linear waveguide, and wherein the first row of nanowells is in phase with the second row of nanowells, the flowcell further comprising: a third linear waveguide that is parallel and adjacent to the second linear waveguide; and a third row of nanowells extending along the third linear waveguide, wherein the third row of nanowells is out of phase with the first and second rows of nanowells. The flowcell further comprises: a fourth linear waveguide that is parallel and adjacent to the third linear waveguide; and a fourth row of nanowells extending along the fourth linear waveguide, wherein the fourth row of nanowells is in phase with the third row of nanowells. The first and second linear waveguides are parallel and adjacent each other, wherein the first set of nanowells comprises first and second rows of nanowells extending along the first linear waveguide on opposite sides thereof, and wherein the second set of nanowells comprises third and fourth rows of nanowells extending along the second linear waveguide on opposite sides thereof. At least one nanowell of the first and second sets of nanowells has a non-circular opening. The non-circular opening comprises an elliptical opening. The flowcell further comprises structure between the first and second linear waveguides to reduce cross-coupling. The structure comprises a series of blocks. The structure provides refractive indices that alternate along the structure. The first linear waveguide and the first grating are positioned in a first layer of the flowcell, wherein the second linear waveguide and the second grating are positioned in a second layer of the flowcell, wherein the first and second sets of nanowells are positioned in a third layer of the flowcell, and wherein the second layer is positioned further from the third layer than is the first layer.

In a second aspect, a method comprises: applying, at a flowcell, a sample to a first set of nanowells and to a second set of nanowells; differentially coupling, using a first grating, first light into at least a first linear waveguide associated with the first set of nanowells; and differentially coupling, using a second grating, second light into at least a second linear waveguide associated with the second set of nanowells.

Implementations can include any or all of the following features. The first and second gratings are spatially offset from each other, the method further comprising controlling an illumination component regarding at least one of the first light or the second light. Controlling the illumination component comprises controlling a beam parameter of a light beam generating at least one of the first light or the second light. Controlling the beam parameter comprises at least one selected from the group consisting of: controlling a location of the light beam, controlling an angle of incidence of the light beam, controlling a divergence of the light beam, controlling a mode profile of the light beam, controlling a polarization of the light beam, controlling an aspect ratio of the light beam, controlling a diameter of the light beam, controlling a wavelength of the light beam, and combinations thereof. The first light is being differentially coupled during a first scan performed across the flowcell in a first scan direction, and the second light is being differentially coupled during a second scan performed across the flowcell in a second scan direction opposite to the first scan direction. The first and second gratings have different grating periods from each other, the method further comprising arranging an illumination component so that the first light is differentially coupled, and arranging the illumination component so that the second light is differentially coupled. The first and second linear waveguides are positioned adjacent each other, and wherein the flowcell further comprises a third linear waveguide positioned adjacent to the second linear waveguide opposite from the first linear waveguide. The flowcell further comprises a third grating for the third linear waveguide. The method further comprises differentially coupling the first light also into the third linear waveguide using the third grating. The method further comprises differentially coupling third light into at least the third linear waveguide using the third grating. The third linear waveguide shares the first grating with the first linear waveguide. The nanowells in at least one of the first and second sets of nanowells have a spacing from each other that is resolvable according to a resolution distance of emission optics for the flowcell. The first and second linear waveguides are positioned closer to each other than the resolution distance of the emission optics. Differentially coupling the first light comprises coupling the first light into the first linear waveguide and minimizing coupling of the first light into the second linear waveguide. Differentially coupling the second light comprises coupling the second light into the second linear waveguide and minimizing coupling of the second light into the first linear waveguide.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

DETAILED DESCRIPTION

Figure 1:
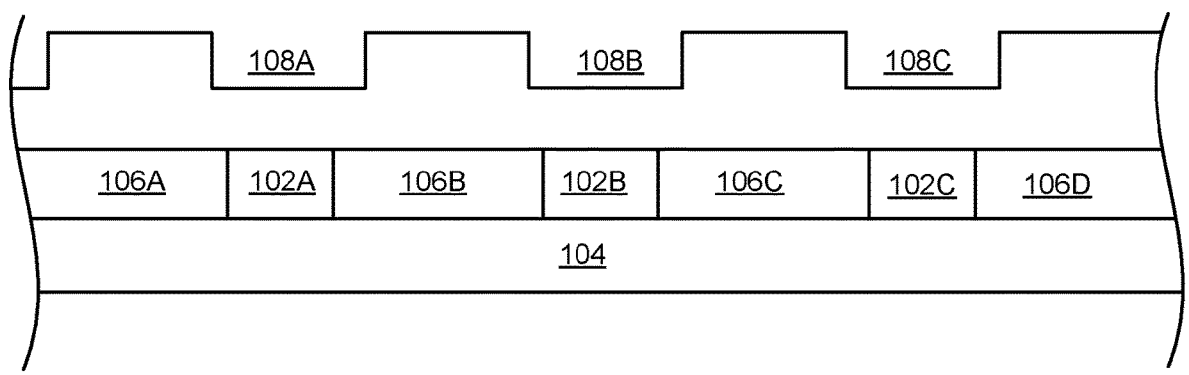
FIG. 1 shows a cross section of part of an example flowcell with linear waveguides.

The present disclosure describes systems, techniques, articles of manufacture, and/or compositions of matter that facilitate improved analysis of samples. In some implementations, differential coupling can be provided into two or more linear waveguides. For example, being able to differentially couple light into linear waveguides can allow a substrate (e.g., a layer of nanowells for holding sample material) to have an increased density of the sample material. In some implementations, one or more parameters regarding the analysis system and/or the process can be selected or adjusted so as to obtain differential coupling. For example, such parameter(s) can include one or more beam parameters, one or more coupler parameters, one or more waveguide parameters, or combinations thereof.

In some implementations, analysis imaging can be performed upon sample material having an increased density of distribution on a substrate, which can increase the throughput of the analysis process. For example, sample material can be distributed with a density where individual portions of the sample are positioned at closer distances from each other than can be resolved using the available imaging technology, such as microscopy equipment. An analysis process may selectively image only first portions of the sample at a time, and not image second portions near the first portions, and subsequently image the second portions without (again) imaging the first portions. Such an approach can allow a relatively large amount of sample material on a single sample holder (e.g., a substrate) to be imaged and analyzed in a single session. This can increase the throughput of the analysis process compared to an approach where the substrate is exchanged after analysis of its entire sample material in order to analyze additional sample material on a new substrate, which approach may involve intermediate steps of substrate removal and insertion, sample preparation, and equipment initialization.

In some implementations, differential coupling between, say, first and second linear waveguides can include coupling light into the first linear waveguide while not coupling any of the light into the second linear waveguide, or vice versa. Such differential coupling may not always be practical or possible. In some implementations, differential coupling can involve minimizing the coupling into, say, the second linear waveguide while coupling the light into the first linear waveguide during a portion of the scan. The amount or fraction of the minimization can differ depending on the implementation. In some implementations, the minimized coupling (e.g., the cross-talk) corresponds to at most about 1%, about 5%, about 15%, about 25% or about 45% of the coupling into the linear waveguide. Such differential coupling may not always be practical or possible. In some implementations, differential coupling can involve reducing the coupling into, say, the second linear waveguide compared to the first linear waveguide during a portion of the scan. The amount or fraction of the reduction can differ depending on the implementation. In some implementations, the reduced coupling (e.g., the cross-talk) corresponds to at most about 5%, about 15%, about 35%, about 65% or about 95% of the coupling into the linear waveguide.

The amount of cross-talk (e.g., the magnitude thereof) may be known or calibrated. In some implementations, multiple scans of a sample can be performed, such as a first scan with coupling into the first linear waveguide where coupling into the second linear waveguide is reduced, and a second scan with coupling into the second linear waveguide where coupling into the first linear waveguide is reduced. The scans may cause modulation of the information obtained from the first and second linear waveguides, respectively. Such modulation may occur in a predictable way given the magnitude of the cross-talk. For example, linear algebra can be applied to the information obtained from the respective first and second linear waveguides to extract useful analysis information.

The limit imposed by the maximum available resolution of imaging equipment can be referred to as a diffraction limit. An imaging system operating at the maximum resolution thus available can be said to be diffraction-limited. For microscopic instruments the spatial resolution that can be obtained given the diffraction limit depends on the light wavelength and on the numerical aperture of the objective or the illumination source. The minimum resolvable distance d can be expressed as $d=\lambda/(2n \sin \theta)$, where $\lambda$ is the wavelength, n is the refractive index, and $\theta$ is the half-angle (i.e., one half of the angle between a microscope optical axis and the direction of the most oblique light rays captured by the objective). The factor $n \sin \theta$ is usually referred to as the numerical aperture (NA), and the minimum resolvable distance can therefore be expressed as $d=\lambda/(2NA)$. That is, in existing analysis systems the sample material is generally distributed with a density such that the individual portions of the sample are at least a distance d apart. Systems and techniques described herein can allow analysis to be performed on sample material that is distributed more densely than the resolution distance d.

Sample analysis can include, but is not limited to, genetic sequencing (e.g., determining the structure of genetic material), genotyping (e.g., determining differences in an individual's genetic make-up), gene expression (e.g., synthesizing a gene product using gene information), proteomics (e.g., large-scale study of proteins), or combinations thereof.

Some examples described herein relate to sequencing of genetic material. Sequencing can be performed on a sample to determine which building blocks, called nucleotides, make up the particular genetic material that is in the sample. The sequencing can be done after the genetic material has first been purified and then replicated a number of times so as to prepare a sample of a suitable size. Imaging can be performed as part of the process of sequencing the genetic material. This can involve fluorescent imaging, where a sample of genetic material is subjected to light (e.g., a laser beam) to trigger a fluorescent response by one or more markers on the genetic material. Some nucleotides of the genetic material can have fluorescent tags applied to them, which allows for determination of the presence of the nucleotide by shining light onto, and looking for a characteristic response from, the sample. Fluorescent responses can be detected over the course of the sequencing process and used to build a record of nucleotides in the sample.

Examples described herein refer to flowcells. A flowcell can be considered a substrate that can be used in preparing and accommodating or carrying one or more samples in at least one stage of an analysis process. The flowcell is made of a material that is compatible with both the sample material (e.g., genetic material), the illumination and the chemical reactions to which it will be exposed. The substrate can have one or more channels in which sample material can be deposited. A substance (e.g., a liquid) can be flowed through the channel where the sample genetic material is present to trigger one or more chemical reactions and/or to remove unwanted material. The flowcell may enable the imaging by facilitating that the sample in the flowcell channel can be subjected to illuminating light and that any fluorescent responses from the sample can be detected. Some implementations of the system may be designed to be used with at least one flowcell, but may not include the flowcell(s) during one or more stages, such as during shipping or when delivered to a customer. For example, the flowcell(s) can be installed into an implementation at the customer's premises in order to perform analysis.

Examples herein refer to coupling of light (e.g., a laser beam) into and/or out of a waveguide by one or more gratings. A grating can couple light impinging on the grating by way of diffracting at least a portion of the light, thereby causing the portion of the light to propagate in one or more other directions. In some implementations, the coupling can involve one or more interactions, including, but not limited to, reflection, refraction, diffraction, interference, and/or transmission of the portion of the light. Implementations may be designed to meet one or more requirements, including, but not limited to, those regarding mass production, cost control, and/or high light coupling efficiency. Two or more gratings can be identical or similar to each other, or different types of gratings can be used. The grating(s) can include one or more forms of periodic structure. In some implementations, the grating can be formed by removing or omitting material from a substrate (e.g., from a waveguide material that is included in the flowcell) or other material. For example, the flowcell can be provided with a set of slits and/or grooves therein to form the grating. In some implementations, the grating can be formed by adding matter to the flowcell (e.g., to a waveguide material that is included in the flowcell) or other material. For example, the flowcell can be provided with a set of ridges, bands or other protruding longitudinal structures to form the grating. Combinations of these approaches can be used.

Providing a waveguide in a substrate (such as a flowcell) can provide one or more advantages. Excitation using evanescent light based on total internal reflection (TIR) can provide a higher efficiency of illumination. In some previous approaches, the entirety of a laser beam was used for illuminating the substrate that held the sample, such as in a scanning process. Such an approach may cause a majority of the light wave simply propagates through the substrate without effectively illuminating the sample. As a result, only a small portion of the light applied by such systems may actually be used for exciting fluorophores in the sample. The evanescent light, by contrast, may penetrate material (e.g., a cladding adjacent to the core layer) only to a certain depth (e.g., about 150-200 nm in one example). For example, the flowcell can be designed with one or more nanowells configured so that the evanescent field is largely confined to the well area. As a result, evanescent light may be a very efficient way of exciting fluorophores. For example, a system operating according to an earlier illumination approach may involve a laser with a certain power; using evanescent light, by contrast, a significantly lower laser power may be sufficient.

Examples herein refer to chemical vapor deposition. Chemical vapor deposition (CVD) may include all techniques where a volatile material (sometimes referred to as a precursor) is caused to undergo reaction and/or decomposition on the surface of a substrate, forming a deposit thereon. CVD may be characterized by one or more aspects. For example, CVD may be characterized by the physical characteristic(s) of the vapor (e.g., whether the CVD is aerosol-assisted or involves direct liquid injection). For example, CVD may be characterized by the type of substrate heating (e.g., whether the substrate is directly heated or indirectly heated, such as by a heated chamber). Examples of types of CVD that can be used include, but are not limited to, atmospheric pressure CVD, low pressure CVD, very low pressure CVD, ultrahigh vacuum CVD, metalorganic CVD, laser assisted CVD, and plasma-enhanced CVD.

Examples herein refer to atomic layer deposition. Atomic layer deposition may be considered a form of CVD and include all techniques where a film is grown on a substrate by exposure to gases. For example, gaseous precursors may be alternatingly introduced into a chamber. The molecules of one of the precursors may react with the surface until a layer is formed and the reaction is terminated, and the next gaseous precursor may then be introduced to begin forming a new layer, and so on in one or more cycles.

Examples herein refer to spray coating. Spray coating may include any or all techniques by which a particularized material is caused to be deposited onto a substrate. This may include, but is not limited to, thermal spraying, plasma spraying, cold spraying, warm spraying, and/or other procedures involving atomized or nebulized material.

Examples herein refer to spin coating. Spin coating may include application of an amount of coating material to a substrate, and distributing or spreading the coating material over the substrate by way of centrifugal force due to rotation or spinning of the substrate.

Examples herein refer to nanoimprinting. In nanoimprinting lithography, a pre-fabricated nanoscale template may mechanically displace a fluidic resin to mold the desired nanostructures. The resin may then be cured with the nanoscale template in place. Following the removal of the nanoscale template, a molded solid resin attached to a desired substrate may be produced. In some implementations, a nanoimprinting process may begin with fully or partially covering a substrate or wafer with imprinting resin (e.g., a resin as exemplified below). One or more nanostructures may be formed in the imprinting resin in a molding process using a nanoscale template. The imprinting resin can be cured against the substrate or wafer, and a resin-removal process can be applied to remove residue from the wafer or substrate. For example, the resin removal can form chamber lanes adjacent to the nanostructures. The substrate or wafer so formed can have another substrate or a gasket applied thereto so as to form a flowcell having the described nanostructures as well as flowcell chambers formed by enclosing the chamber lanes. In some implementations, the process of applying the imprinting resin may be configured to produce little or no resin residue, and in such implementations a resin-removal process can be omitted. In some applications, the cured resin may also be functionalized with a chemical treatment or an attachment of biomolecules, depending on the end use. In nanoimprinting lithography, an imprinted photoresist can be a sacrificial material and similarly be used as an intermediate tool to transfer the patterned resist into the substrate or a variation of the resist can be used such that the imprinted resist serves as the input to a subsequent coating step. An example of a resist that would remain following patterning is material formed by a process that involves conversion of monomers into a colloidal solution as a precursor to a gel of particles and/or polymers, sometimes referred to as a sol-gel based material.

Examples herein refer to substrates. A substrate may refer to any material that provides an at least substantially rigid structure, or to a structure that retains its shape rather than taking on the shape of a vessel to which it is placed in contact. The material can have a surface to which another material can be attached including, for example, smooth supports (e.g., metal, glass, plastic, silicon, and ceramic surfaces), as well as textured and/or porous materials. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Examples herein refer to polymers. A polymer layer can include a film of a polymer material. Example film forming polymers include, without limitation, acrylamide or copolymers with C1-C12; aromatic and hydroxyl derivatives; acrylate copolymers; vinylpyrrolidine and vinylpyrrolidone copolymers; sugar based polymers such as starch or polydextrins; or other polymers such as polyacrylic acid, polyethylene glycol, polylactic acid, silicone, siloxanes, polyethyleneamines, guar gum, carrageenan, alginate, lotus bean gum, methacrylate co polymers, polyimide, a cyclic olefin copolymer, or combinations thereof. In some implementations, a polymer layer comprises at least one photocurable polymer. For example, a photocurable polymer can include urethane, acrylate, silicone, epoxy, polyacrylic acid, polyacrylates, epoxysilicone, epoxy resins, polydimethylsiloxane (PDMS), silsesquioxane, acyloxysilanes, maleate polyesters, vinyl ethers, monomers with vinyl or ethynyl groups, or copolymers, or combinations thereof. In some implementations, a layer can include a covalently attached polymer coating. For example, this can include a polymer coating that forms chemical bonds with a functionalized surface of a substrate, as compared to attachment to the surface in other ways, for example, adhesion or electrostatic interaction. In some implementations, a polymer comprised in a functionalizable layer is poly(N-(5-azidoacetamidylpentyl) acrylamide-co-acrylamide), sometimes referred to as PAZAM.

Examples described herein mention that one or more resins may be used. Any suitable resin may be used for nanoimprinting in methods described herein. In some implementations, an organic resin may be used, including, but not limited to, an acrylic resin, a polyimide resin, a melamine resin, a polyester resin, a polycarbonate resin, a phenol resin, an epoxy resin, polyacetal resin, polyether resin, polyurethane resin, polyamide resin (and/or nylon), a furan resin, a diallylphthalate resin, or combinations thereof. In some examples, a resin may include an inorganic siloxane polymer including a Si—O—Si bond among compounds (including silicon, oxygen, and hydrogen), and formed by using a siloxane polymer-based material typified by silica glass as a starting material. A resin used may also or instead be an organic siloxane polymer in which hydrogen bonded to silicon is substituted by an organic group, such as methyl or phenyl, and typified by an alkylsiloxane polymer, an alkylsilsesquioxane polymer, a silsesquioxane hydride polymer, or an alkylsilsesquioxane hydride polymer. Non-limiting examples of siloxane polymers include polyhedral oligomeric silsesquioxane (POSS), polydimethylsiloxane (PDMS), tetraethyl ortho silicate (TEOS), poly (organo) siloxane (silicone), and perfluoropolyether (PFPE). A resin may be doped with a metal oxide. In some implementations, a resin may be a sol-gel material including, but not limited to, titanium oxide, hafnium oxide, zirconium oxide, tin oxide, zinc oxide, or germanium oxide, and that uses a suitable solvent. Any one of a number of other resins may be employed, as appropriate to the application.

FIG. 1 shows a cross section of part of an example flowcell 100 with linear waveguides 102A-102C. The flowcell 100 can be used with one or more methods described herein, and/or be used in combination with one or more systems or apparatuses described herein. Only a portion of the flowcell 100 is shown, for purposes of illustration. For example, one or more additional layers and/or more or fewer waveguides 102A-102C, can be used.

The flowcell 100 includes a substrate 104. The substrate 104 can form a base for the flowcell 100. In some implementations, one or more other layers can be formed at (e.g., in contact with or near) the substrate 104 in the manufacturing of the flowcell 100. The substrate 104 can serve as a basis for forming the linear waveguides 102A-102C. The linear waveguides 102A-102C can initially exist separately from the substrate 104 and thereafter be applied onto the substrate 104, or the linear waveguides 102A-102C can be formed by application, and/or removal of, one or more materials to or from the substrate. The linear waveguides 102A-102C can be formed directly onto the substrate 104, or onto one or more intermediate layers at the substrate 104.

The linear waveguides 102A-102C serve to conduct electromagnetic radiation (including, but not limited to, visible light, such as laser light). In some implementations, the electromagnetic radiation performs one or more functions during an imaging process. For example, the electromagnetic radiation can serve to excite fluorophores in a sample material for imaging. The linear waveguides 102A-102C can be made of any suitable material that facilitates propagation of one or more kinds of electromagnetic radiation. In some implementations, the material(s) of the linear waveguides 102A-102C can include a polymer material. In some implementations, the material(s) of the linear waveguides 102A-102C can include $Ta_2O_5$ and/or $SiN_x$. For example, the linear waveguides 102A-102C can be formed by sputtering, chemical vapor deposition, atomic layer deposition, spin coating, and/or spray coating.

Each of the linear waveguides 102A-102C can have one or more gratings (omitted here for clarity) to couple electromagnetic radiation into and/or out of that linear waveguide 102A-102C. One or more directions of travel for the electromagnetic radiation in the linear waveguides 102A-102C can be employed. For example, the direction of travel can be into and/or out of the plane of the present illustration. Examples of gratings are described elsewhere herein.

Each of the linear waveguides 102A-102C can be positioned against one or more types of cladding. The cladding can serve to constrain the electromagnetic radiation to the respective linear waveguide 102A-102C and prevent, or reduce the extent of, propagation of the radiation into other linear waveguides 102A-102C or other substrates. Here, claddings 106A-106D are shown as an example. For example, the claddings 106A-106B can be positioned against or near the linear waveguide 102A on different (e.g., opposing) sides thereof. For example, the claddings 106B-106C can be positioned against or near the linear waveguide 102B on different (e.g., opposing) sides thereof. For example, the claddings 106C-106D can be positioned against or near the linear waveguide 102C on different (e.g., opposing) sides thereof. The claddings 106A-106D can be made from one or more suitable materials that serve to separate the linear waveguides 102A-102C from each other. In some implementations, the claddings 106A-106D can be made from a material having a lower refractive index than the refractive index/indices of the linear waveguides 102A-102C. For example, the linear waveguides 102A-102C can have a refractive index of about 1.4-1.6, and the claddings 106A-106D can have a refractive index of about 1.2-1.4. In some implementations, one or more of the claddings 106A-106D includes a polymer material. In some implementations, one or more of the claddings 106A-106D includes multiple structures, including, but not limited to, structures of one material (e.g., polymer) interspersed by regions of vacuum or another material (e.g., air or a liquid).

The flowcell 100 includes at least one nanowell layer 108. In some implementations, the nanowell layer 108 is positioned opposite the linear waveguides 102A-102C from the substrate 104. For example, the nanowell layer can be positioned adjacent (e.g., abutting or near) the linear waveguides 102A-102C and the claddings 106A-106D. The nanowell layer 108 includes one or more nanowells. In some implementations, the nanowell layer 108 includes nanowells 108A-108C. The nanowells 108A-108C can be used for holding one or more sample materials during at least part of the analysis process (e.g., for imaging). For example, one or more genetic materials (e.g., in form of clusters) can be placed in the nanowells 108A-108C.

One or more of the nanowells 108A-108C can be at least substantially aligned with one or more of the linear waveguides 102A-102C. This can allow interaction between the respective nanowell 108A-108C and the corresponding linear waveguide 102A-102C for imaging purposes (including, but not limited to, by way of transmission of evanescent light). For example, the nanowell 108A can be at least substantially aligned with the linear waveguide 102A; the nanowell 108B can be at least substantially aligned with the linear waveguide 102B; and/or the nanowell 108C can be at least substantially aligned with the linear waveguide 102C.

The nanowells 108A-108C can be formed by nanoimprinting into the nanowell layer 108, or a lift-off process from the nanowell layer 108. For example, the nanowell layer 108 can include a resin and the nanowells 108A-108C can be formed by imprinting using a nanoscale template. In some implementations, the nanowells 108A-108C can have a size such that one or more of its dimensions ranges in the order of one or more nanometers. An end (e.g., the bottom) of the nanowells 108A-108C can have a thickness that accommodates propagation of evanescent light. For example, the thickness can be about 0-500 nm. The nanowell layer can cover at least substantially the entire facing surface of the layer that includes the linear waveguides 102A-102C and the claddings 106A-106D. In some implementations, the nanowell layer 108 can have an average pitch between the nanowells 108A-108C of at least 10 nm, 0.1 μm, 0.5 μm, 1 μm, 5 μm, 10 μm, 100 μm or more, and/or can have an average pitch of at most 100 μm, 10 μm, 5 μm, 0.5 μm 0.1 μm or less. In some implementations, the nanowell layer 108 can have a pitch between the nanowells 108A-108C of about 150 nm or greater. For example, the nanowell layer 108 can have a pitch between the nanowells 108A-108C of about 160 nm, 220 nm, 250 nm, 300 nm, 450 nm, or greater. The depth of each nanowell 108A-108C can be at least 0.1 μm, 10 μm, 100 μm or more. Alternatively or additionally, the depth can be at most $1\times10^3$ μm, 100 μm, 10 μm, 0.1 μm or less.

Figure 2:
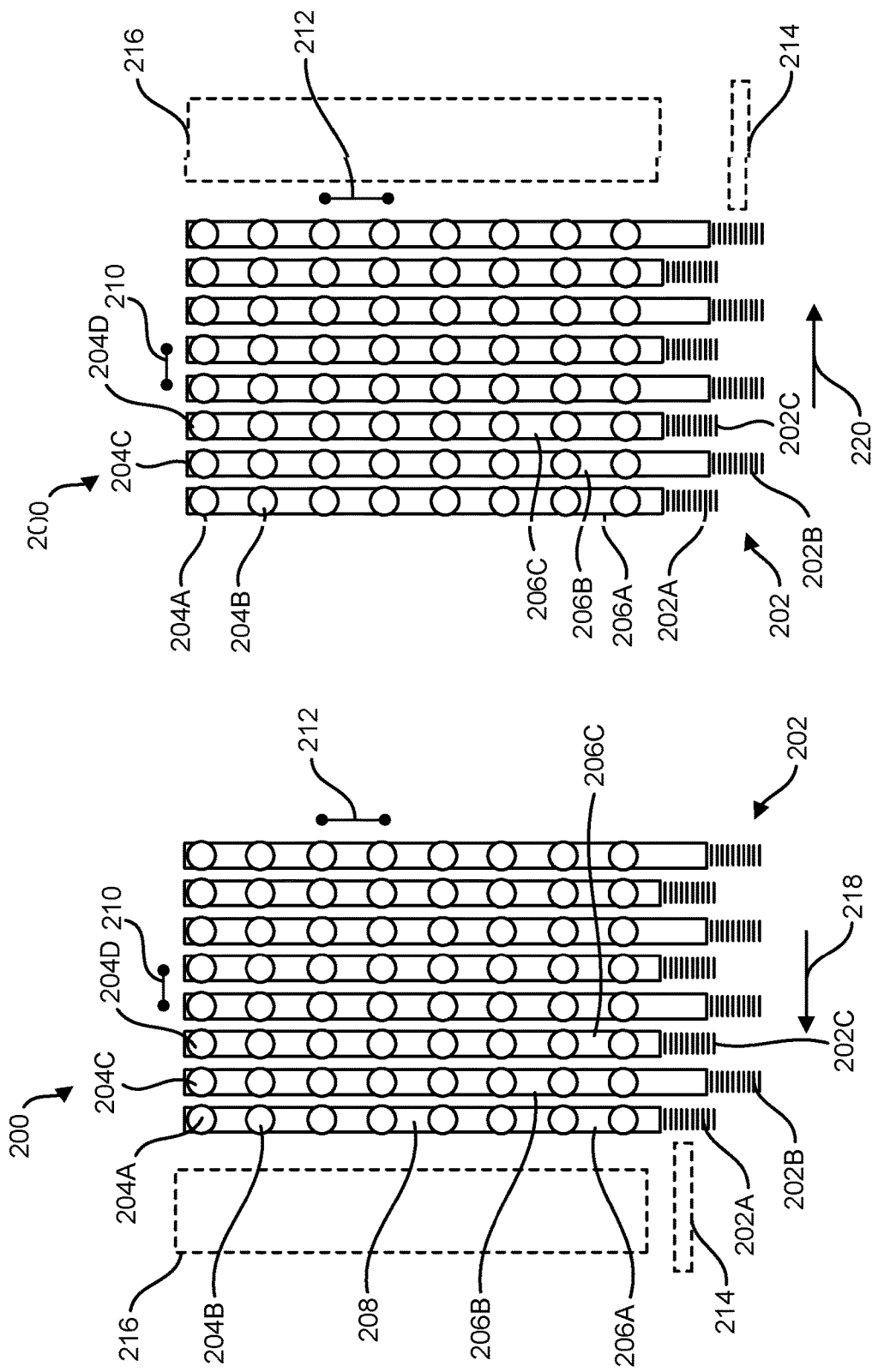
FIGS. 2A-2B illustrate examples with a flowcell having staggered gratings.

FIGS. 2A-2B illustrate examples with a flowcell 200 having staggered gratings 202. The flowcell 200 can be used with one or more methods described herein, and/or be used in combination with one or more systems or apparatuses described herein. Only a portion of the flowcell 200 is shown, for purposes of illustration.

The flowcell 200 includes nanowells, including a nanowell 204A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 204A is here associated with a linear waveguide 206A. In some implementations, the linear waveguides described with reference to the flowcell 200 can be similar or identical to one or more other linear waveguides described herein. For example, the linear waveguide 206A is positioned adjacent (e.g., in contact with or near) the nanowell layer that includes the nanowell 204A. In some implementations, the linear waveguide 206A can include a linear waveguide core 208 and one or more of the gratings 202.

Another nanowell 204B is also associated with the linear waveguide 206A. For example, the nanowell 204B is positioned adjacent to the nanowell 204A and both of the nanowells 204A-204B can interact with the linear waveguide 206A in an imaging process (e.g., by way of receiving electromagnetic radiation from the linear waveguide 206A). Another nanowell 204C, by contrast, is instead associated with a linear waveguide 206B. In some implementations, the linear waveguide 206B is positioned adjacent to the linear waveguide 206A. For example, cladding (not shown) and/or another material can be positioned between the linear waveguides 206A-206B.

Some examples described herein mention or otherwise relate to sets of nanowells. A set of nanowells is a logical or physical group of one or more nanowells having at least one characteristic. A set of nanowells may be associated with one linear waveguide, and another set of nanowells may be associated with another linear waveguide. In some implementations, a set of nanowells may be arranged in a row. Such a row of nanowells can extend along the linear waveguide, such as by being coextensive with (e.g., fully overlapping above or below) the linear waveguide, or by being parallel to and positioned adjacent (e.g., on either or both sides of) the linear waveguide, to name just some examples. Accordingly, a set of nanowells can include one or more rows of nanowells in some implementations. Each of such rows of nanowells can be aligned with at least one linear waveguide.

Nanowells can be arranged on a substrate (e.g., in a nanowell layer) in a substantially, and in at least one instance completely, random way or according to one or more patterns. In some implementations, the nanowells are arranged in form of one or more arrays, including, but not limited to, a polygonal array. For example, a polygonal array can be a rectangular, triangular, or a hexagonal array, or any other form of array where at least some nanowells are arranged in a polygon shape. The flowcell 200 in this example has a rectangular array of nanowells.

The flowcell 200 can be used in one or more forms of imaging process. For example, sample material in the nanowells (including the nanowells 204A-204C) can be subjected to electromagnetic radiation from respective linear waveguides (including the linear waveguides 206A-206B, respectively). Emissions resulting from such exposure to electromagnetic radiation (an example of emissions being fluorescence from fluorophores) can be captured using equipment (e.g., one or more cameras and/or other imaging devices). Such equipment is sometimes referred to by way of the expression emission equipment or a similar term. For example, emission equipment can include one or more cameras or other image sensors and at least one lens or other emission optics. In some implementations, the diffraction limit can be at least partially attributable to one or more characteristics of the emission optics. For example, based on the emission optics used, a resolution distance can be defined, the resolution distance marking the shortest distance that can be resolved using the emission optics. That is, when resolving features that are spaced apart by the resolution distance, the imaging system can be said to be operating at its highest available level of resolution.

Here, a distance 210 is less than the resolution distance of the emission optics, and a distance 212 is greater than, or about equal to, the resolution distance of the emission optics. The distance 210 here represents the separation between nanowells in one direction. In some implementations, this can be the direction across the linear waveguides. For example, because the linear waveguides are here aligned with rows of the nanowells in one direction (e.g., the vertical direction as seen in the illustration), the distance 210 can also represent the distance between adjacent linear waveguides (e.g., the linear waveguides 206A-206B). For example, the nanowells 204A and 204C are separated by the distance 210. That is, the linear waveguides 206A-206B are positioned closer to each other than the resolution distance of the emission optics.

The distance 212 here represents the separation between nanowells in another direction than the distance 210. For example, the distances 210 and 212 can be substantially, and in at least one instance completely, perpendicular to each other. In some implementations, this can be the direction along any individual one of the linear waveguides. For example, because the linear waveguides are here aligned with rows of the nanowells in one direction (e.g., the vertical direction as seen in the illustration), the distance 212 can represent the distance between adjacent nanowells on any of the linear waveguides (e.g., the linear waveguides 206A-206B). For example, the nanowells 204A and 204B are separated by the distance 212. That is, the nanowells associated with the linear waveguide 206A have a spacing from each other that is resolvable according to the resolution distance of emission optics for the flowcell 200.

The gratings 202 serve for coupling electromagnetic radiation into and/or out of the linear waveguides of the flowcell 200. Here, the linear waveguide 206A has a grating 202A and the linear waveguide 206B has a grating 202B. The gratings 202A-202B can have the same or different periodic structure. In some implementations, either or both of the gratings 202A-202B can include a periodic structure of ridges interspersed by another material. For example, ridges of the gratings 202A-202B can have a pitch of about 200-300 nm, to name just one example.

The gratings 202A-202B can have one or more characteristics that facilitate selective coupling of electromagnetic radiation into the corresponding linear waveguide 206A-206B. In some implementations, one or more of the gratings 202 is spatially offset from one or more others of the gratings 202. The offset can be in a direction that is parallel to the linear waveguides 206A-206B. For example, the distance between the grating 202B and the closest nanowell of the nanowells associated with the linear waveguide 206B is here greater than the distance between the grating 202A and the closest nanowell of the nanowells associated with the linear waveguide 206A. The characteristic of the gratings 202A-202B being spatially offset from each other facilitates coupling of electromagnetic radiation (e.g., light) into one of the linear waveguides (e.g., the linear waveguide 206A) without coupling the electromagnetic radiation (e.g., light) into another of the linear waveguides (e.g., the linear waveguide 206B).

The flowcell 200 can include multiple linear waveguides, for example as illustrated. In some implementations, a linear waveguide 206C is positioned adjacent to the linear waveguide 206B opposite from the linear waveguide 206A. For example, the linear waveguide 206C can have a grating 202C. In some implementations, the grating 202C can be spatially offset from the grating 202B. For example, the grating 202C can have the same spatial offset from the grating 202B, in the direction parallel to the linear waveguide 206C, as the grating 202A has in the direction parallel to the linear waveguide 206A.

The characteristic of the gratings 202A and 202C being spatially offset from the grating 202B facilitates coupling of electromagnetic radiation (e.g., light) into one of the linear waveguides (e.g., the linear waveguide 206A or 206C) without coupling the electromagnetic radiation (e.g., light) into another of the linear waveguides (e.g., the linear waveguide 206B). As another example, the characteristic facilitates coupling of electromagnetic radiation (e.g., light) into one of the linear waveguides (e.g., the linear waveguide 206B) without coupling the electromagnetic radiation (e.g., light) into at least one other of the linear waveguides (e.g., the linear waveguide 206A or 206C).

A light area 214 is here schematically illustrated as a rectangle with a dashed outline. The light area 214 represents one or more positions where light or other electromagnetic radiation is caused to impinge as part of an imaging process. In some implementations, illuminating light generated by a laser can be directed at the light area 214 in order to eventually be coupled into some of the linear waveguides. For example, the laser light can be selected so as to correspond to fluorescence properties of one or more fluorophores in the sample material.

An image capture area 216 is here schematically illustrated as a rectangle with a dashed outline. The image capture area 216 represents the field of view of the emission optics. For example, a camera or other image sensor can capture one or more types of emissions (e.g., fluorescent light) emanating from the image capture area 216.

The examples described above illustrate that the flowcell 200 includes a nanowell layer having first (e.g., the nanowells associated with the linear waveguide 206A) and second (e.g., the nanowells associated with the linear waveguide 206B) sets of nanowells to receive a sample. The flowcell 200 includes a first linear waveguide (e.g., the linear waveguide 206A) aligned with the first set of nanowells, and a second linear waveguide (e.g., the linear waveguide 206B) aligned with the second set of nanowells; and a first grating (e.g., the grating 202A) for the first linear waveguide, and a second grating (e.g., the grating 202B) for the second linear waveguide. The first grating has a first characteristic (e.g., being spatially offset from the grating 202B) to facilitate coupling of first light into the first linear waveguide without coupling the first light into the second linear waveguide.

An image capture process can include one or more scanning operations. In some implementations, the image capture area 216 can be caused to overlay one or more areas of the flowcell 200 to facilitate image capture regarding one or more nanowells in the image capture area 216. The positioning can include movement of the image capture area 216, or the flowcell 200, or both. For example, the emission optics can be relatively stationary in the analysis equipment, such that the image capture area 216 does not move during various scanning operations. For example, the flowcell 200 can be moved (e.g., by being positioned on a motorized stage that facilitates precise movement in at least one direction) relative to the image capture area 216 into one or more scanning positions. Here, an arrow 218 schematically illustrates that the flowcell 200 can be moved so that the image capture area 216 overlays at least some of the linear waveguides and the nanowells associated with them.

The light area 214 can remain stationary with, or be moved corresponding to, or be moved independently of, the image capture area 216. In this example, the light area 214 is aligned with some of the gratings 202 (e.g., with the gratings 202A and 202C) but is not aligned with some other ones of the gratings (e.g., with the grating 202B). For example, when scanning is done in the direction of the arrow 218 with the current position of the light area 214, the gratings 202A and 202C (and others having similar spatial offset) will be illuminated by the light impinging at the light area 214, whereas some other ones of the gratings (e.g., the grating 202B) will not be illuminated by the light impinging at the light area 214. Accordingly, illuminating light will be coupled into the linear waveguides 206A and 206C (and others whose gratings have similar spatial offsets), whereas the light will not be coupled into the linear waveguide 206B (and others whose gratings have similar spatial offsets). This can facilitate a selective illumination of the nanowells of the flowcell 200. For example, because the linear waveguides 206A and 206C have light coupled into them, excitation light can reach the nanowells 204A and 204C associated with the linear waveguide 206A, and a nanowell 204D associated with the linear waveguide 206C. On the other hand, excitation light should not reach the nanowell 204C because it is associated with the linear waveguide 206B which does not currently have light coupled into it. As such, the imaging can successfully proceed although some portions of the sample material (e.g., within the nanowells 204A and 204C) are positioned at the distance 210 from each other; that is, closer to each other than the resolution distance of the emission optics. During the scanning corresponding to the movement represented by the arrow 218 (which may be characterized as a line scan), only a particular subset of the linear waveguides can have light coupled into them. In some implementations, light is coupled into only every second linear waveguide. For example, light may be coupled into only the first, third, fifth, seventh, and so on, linear waveguide, whereas light is not coupled into the second, fourth, sixth, eighth, and so on, linear waveguide.

In some implementations, the distance 210 is shorter than a diffraction limit (e.g., a resolution distance of the emission optics). For example, if the wavelength is about 700 nm with a 0.75 numerical aperture, the diffraction limit is about 466 nm, and the distance 210 can then be shorter than this limit. In some implementations, the flowcell 200 can be designed so that the nanowells 204A and 204D are separated from each other by about the diffraction limit (e.g., by about 466 nm). For example, the distance 210 can then be about half of the diffraction limit (e.g., about 233 nm). As another example, if the wavelength is about 525 nm with a 0.75 numerical aperture, the diffraction limit is about 350 nm, and the distance 210 can then be about 175 nm. The above example involves activating every other linear waveguide at a time. In some implementations, fewer than every other linear waveguide can be actuated at a time. For example, if every third linear waveguide is activated at a time, then the distance 210 can be about one third of the diffraction limit. As another example, if every fourth linear waveguide is activated at a time, then the distance 210 can be about one fourth of the diffraction limit, and so on.

The scanning being illustrated in FIG. 2A can be described as the flowcell 200 being moved to the left in the image, and stopping at one or more selected positions corresponding to the linear waveguides as the image capture area 216 overlays them, until the flowcell 200 is to the left of the image capture area 216. One or more linear waveguides which do not have light coupled into them during the scan illustrated in FIG. 2A, and whose associated nanowells are accordingly not then subjected to excitation light, can be imaged in another scanning operation.

Such other scanning operation can be performed in the same direction as described above (e.g., along the direction of the arrow 218) or in another direction. FIG. 2B shows an example where scanning is done along a direction corresponding to an arrow 220, which direction is substantially, and in at least one instance completely, opposite to the direction associated with the arrow 218. The scanning being illustrated in FIG. 2B can be described as the flowcell 200 being moved to the right in the image, and stopping at one or more selected positions corresponding to the linear waveguides as the image capture area 216 overlays them, until the flowcell 200 is to the right of the image capture area 216. The positioning can include movement of the image capture area 216, or the flowcell 200, or both.

In this example, the light area 214 is aligned with some of the gratings 202 (e.g., with the grating 202B) but is not aligned with some other ones of the gratings (e.g., with the gratings 202A and 202C). For example, when scanning is done in the direction of the arrow 220 with the current position of the light area 214, the grating 202B (and others having similar spatial offset) will be illuminated by the light impinging at the light area 214, whereas some other ones of the gratings (e.g., the gratings 202A and 202C) will not be illuminated by the light impinging at the light area 214. Accordingly, illuminating light will be coupled into the linear waveguide 206B (and others whose gratings have similar spatial offsets), whereas the light will not be coupled into the linear waveguides 206A and 206C (and others whose gratings have similar spatial offsets). This can facilitate a selective illumination of the nanowells of the flowcell 200. For example, because the linear waveguide 206C has light coupled into it, excitation light can reach the nanowell 204C and others associated with the linear waveguide 206B. On the other hand, excitation light should not reach the nanowells 204A-204B that are associated with the linear waveguide 206A, or the nanowell 204D that is associated with the linear waveguide 206C, which linear waveguides do not currently have light coupled into them. As such, the imaging can successfully proceed although some portions of the sample material (e.g., within the nanowells 204A and 204C) are positioned at the distance 210 from each other; that is, closer to each other than the resolution distance of the emission optics. During the scanning corresponding to the movement represented by the arrow 220 (which may be characterized as a line scan), only a particular subset of the linear waveguides can have light coupled into them. In some implementations, light is coupled into only every second linear waveguide. For example, light may be coupled into only the second, fourth, sixth, eighth, and so on, linear waveguide, whereas light is not coupled into the first, third, fifth, seventh, and so on, linear waveguide.

The examples relating to FIGS. 2A-2B relate to differential coupling where the gratings 202 are spatially offset from each other. In some implementations, one or more other approaches can instead or also be used for differential coupling. Such approaches can include, but are not limited to, differentiated beam parameters, differentiated coupler parameters, and/or differentiated waveguide parameters. Examples are provided below.

Figure 3:
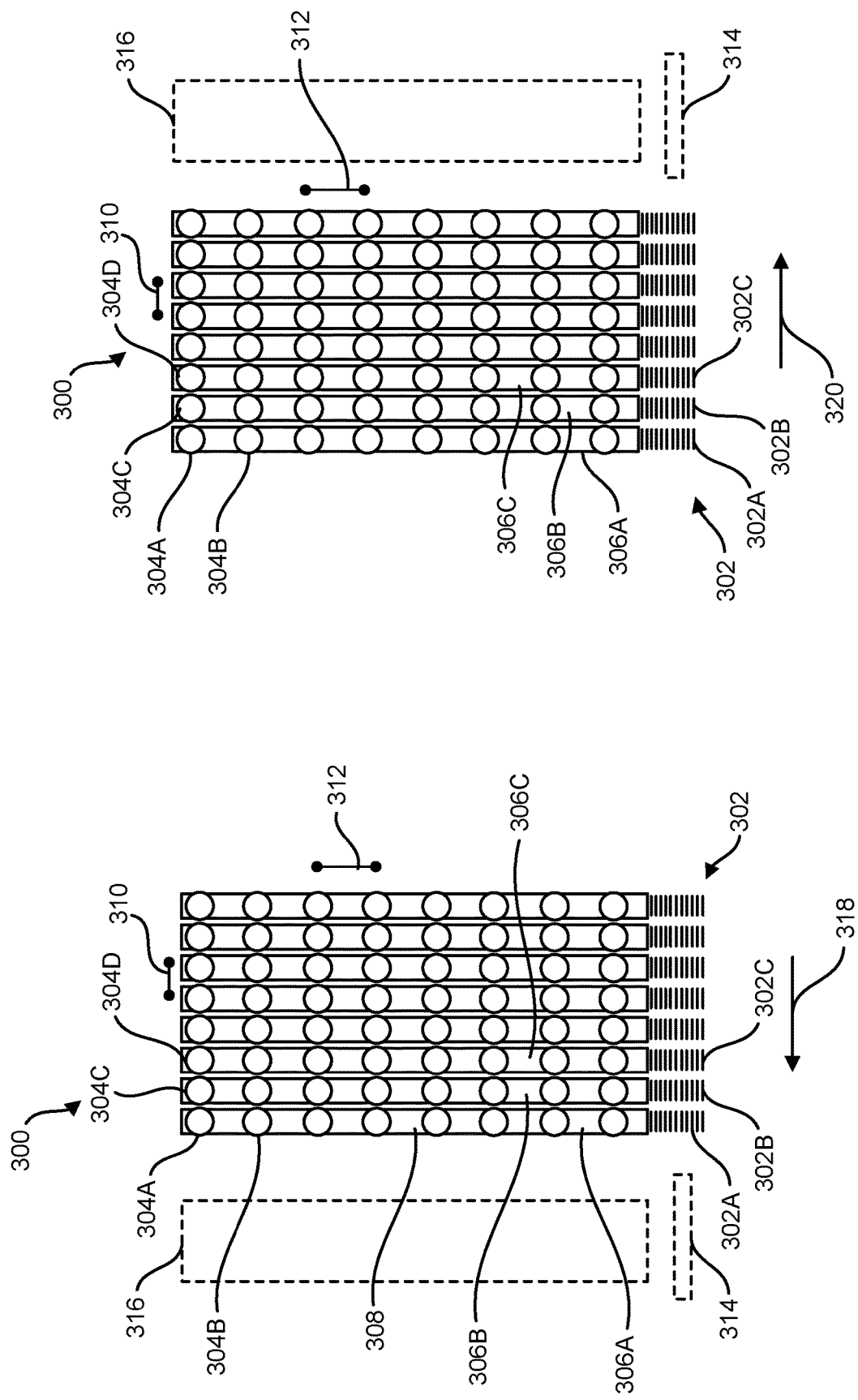
FIGS. 3A-3B illustrate examples with a flowcell having gratings with different grating periods.

FIGS. 3A-3B illustrate examples with a flowcell 300 having gratings 302. In some implementations, differential coupling for the flowcell 300 is provided based on differentiating one or more parameters of the light beam(s) applied to the gratings 302. In some implementations, differential coupling for the flowcell 300 is provided based on differentiating one or more parameters of the gratings 302. In some implementations, differential coupling for the flowcell 300 is provided based on differentiating one or more parameters of the linear waveguides of the flowcell 300. Combinations of two or more of these approaches can be used. The flowcell 300 can be used with one or more methods described herein, and/or be used in combination with one or more systems or apparatuses described herein. Only a portion of the flowcell 300 is shown, for purposes of illustration.

The flowcell 300 includes nanowells, including a nanowell 304A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 304A is here associated with a linear waveguide 306A. In some implementations, the linear waveguides described with reference to the flowcell 300 can be similar or identical to one or more other linear waveguides described herein. For example, the linear waveguide 306A is positioned adjacent (e.g., in contact with or near) the nanowell layer that includes the nanowell 304A. In some implementations, the linear waveguide 306A can include a linear waveguide core 308 and one or more of the gratings 302.

Another nanowell 304B is also associated with the linear waveguide 3206A. For example, the nanowell 304B is positioned adjacent to the nanowell 304A and both of the nanowells 304A-304B can interact with the linear waveguide 306A in an imaging process (e.g., by way of receiving electromagnetic radiation from the linear waveguide 306A). Another nanowell 304C, by contrast, is instead associated with a linear waveguide 306B. In some implementations, the linear waveguide 306B is positioned adjacent to the linear waveguide 306A. For example, cladding (not shown) and/or another material can be positioned between the linear waveguides 306A-306B.

The flowcell 300 can be used in one or more forms of imaging process. For example, sample material in the nanowells (including the nanowells 304A-304C) can be subjected to electromagnetic radiation from respective linear waveguides (including the linear waveguides 306A-306B, respectively). Emissions resulting from such exposure to electromagnetic radiation (an example of emissions being fluorescence from fluorophores) can be captured using equipment (e.g., one or more cameras and/or other imaging devices). Such equipment is sometimes referred to as emission equipment or a similar term. For example, emission equipment can include one or more cameras or other image sensors and at least one lens or other emission optics. In some implementations, the diffraction limit can be at least partially attributable to one or more characteristics of the emission optics. For example, based on the emission optics used, a resolution distance can be defined, the resolution distance marking the shortest distance that can be resolved using the emission optics. That is, when resolving features that are spaced apart by the resolution distance, the imaging system can be said to be operating at its highest available level of resolution.

Here, a distance 310 is less than the resolution distance of the emission optics, and a distance 312 is greater than, or about equal to, the resolution distance of the emission optics. The distance 310 here represents the separation between nanowells in one direction. In some implementations, this can be the direction across the linear waveguides. For example, because the linear waveguides are here aligned with rows of the nanowells in one direction (e.g., the vertical direction as seen in the illustration), the distance 310 can also represent the distance between adjacent linear waveguides (e.g., the linear waveguides 306A-306B). For example, the nanowells 304A and 304C are separated by the distance 310. That is, the linear waveguides 306A-306B are positioned closer to each other than the resolution distance of the emission optics.

The distance 312 here represents the separation between nanowells in another direction than the distance 310. For example, the distances 310 and 312 can be substantially, and in at least one instance completely, perpendicular to each other. In some implementations, this can be the direction along any individual one of the linear waveguides. For example, because the linear waveguides are here aligned with rows of the nanowells in one direction (e.g., the vertical direction as seen in the illustration), the distance 312 can represent the distance between adjacent nanowells on any of the linear waveguides (e.g., the linear waveguides 306A-306B). For example, the nanowells 304A and 304B are separated by the distance 312. That is, the nanowells associated with the linear waveguide 306A have a spacing from each other that is resolvable according to the resolution distance of emission optics for the flowcell 300.

The gratings 302 serve for coupling electromagnetic radiation into and/or out of the linear waveguides of the flowcell 300. Here, the linear waveguide 306A has a grating 302A and the linear waveguide 306B has a grating 302B. The gratings 302A-302B here have different periodic structures. In some implementations, either or both of the gratings 302A-302B can include a periodic structure of ridges interspersed by another material. For example, ridges of the gratings 302A-302B can have a pitch of about 200-300 nm, to name just one example.

The gratings 302A-302B can have one or more characteristics that facilitate selective coupling of electromagnetic radiation into the corresponding linear waveguide 306A-306B. In some implementations, one or more of the gratings 302 has a different grating period from one or more others of the gratings 302. For example, the grating 302A may have a higher grating period than the grating 302B. As another example, the grating 302B may have a higher grating period than the grating 302A. The characteristic of the gratings 302A-302B having different grating periods from each other facilitates coupling of electromagnetic radiation (e.g., light) into one of the linear waveguides (e.g., the linear waveguide 306A) without coupling the electromagnetic radiation (e.g., light) into another of the linear waveguides (e.g., the linear waveguide 306B).

In some implementations, coupling into the gratings 302A-302C can also or instead be differentiated by a coupler parameter other than grating period (e.g., but not limited to, refractive index, pitch, groove width, groove height, groove spacing, grating non-uniformity, groove orientation, groove curvature, overall shape of the coupler, and combinations thereof). In some implementations, coupling into the gratings 302A-302C can also or instead be differentiated by a waveguide parameter regarding one or more linear waveguides of the flowcell 300 (e.g., but not limited to, cross-sectional profile, refractive index difference, mode matching with the coupler and/or beam, and combinations thereof). In some implementations, coupling into the gratings 302A-302C can also or instead be differentiated by a beam parameter of the light beam(s) applied to the flowcell 300 (e.g., but not limited to, location of the light beam, angle of incidence, divergence, mode profile, polarization, aspect ratio, diameter, wavelength, and combinations thereof).

The flowcell 300 can include multiple linear waveguides, for example as illustrated. In some implementations, a linear waveguide 306C is positioned adjacent to the linear waveguide 306B opposite from the linear waveguide 306A. In other words, in this implementation, the linear waveguide 306B is between the linear waveguide 306A and linear waveguide 306C. For example, the linear waveguide 306C can have a grating 302C. In some implementations, the grating 302C can have a different grating period from the grating 302B. For example, the grating 302C can have the same grating period as the grating 302A. As another example, the grating 302C can have a different grating period from the grating 302A and from the grating 302B. The characteristic of at least some of the gratings 302A-302C having different grating periods facilitates coupling of electromagnetic radiation (e.g., light) into one of the linear waveguides (e.g., the linear waveguide 306A or 306C) without coupling the electromagnetic radiation (e.g., light) into another of the linear waveguides (e.g., the linear waveguide 306B). As another example, the characteristic facilitates coupling of electromagnetic radiation (e.g., light) into one of the linear waveguides (e.g., the linear waveguide 306B) without coupling the electromagnetic radiation (e.g., light) into at least one other of the linear waveguides (e.g., the linear waveguide 306A or 306C).

A light area 314 is here schematically illustrated as a rectangle with a dashed outline. The light area 314 represents one or more positions where light or other electromagnetic radiation is caused to impinge as part of an imaging process. In some implementations, illuminating light generated by a laser can be directed at the light area 314 in order to eventually be coupled into some of the linear waveguides. For example, the laser light can be selected so as to correspond to fluorescence properties of one or more fluorophores in the sample material.

An image capture area 216 is here schematically illustrated as a rectangle with a dashed outline. The image capture area 316 represents the field of view of the emission optics. For example, a camera or other image sensor can capture one or more types of emissions (e.g., fluorescent light) emanating from the image capture area 316.

The examples described above illustrate that the flowcell 300 includes a nanowell layer having first (e.g., the nanowells associated with the linear waveguide 306A) and second (e.g., the nanowells associated with the linear waveguide 306B) sets of nanowells to receive a sample. The flowcell 300 includes a first linear waveguide (e.g., the linear waveguide 306A) aligned with the first set of nanowells, and a second linear waveguide (e.g., the linear waveguide 306B) aligned with the second set of nanowells; and a first grating (e.g., the grating 302A) for the first linear waveguide, and a second grating (e.g., the grating 302B) for the second linear waveguide. The first grating has a first characteristic (e.g., having a different grating period from the grating 302B) to facilitate coupling of first light into the first linear waveguide without coupling the first light into the second linear waveguide.

An image capture process can include one or more scanning operations. In some implementations, the image capture area 316 can be caused to overlay one or more areas of the flowcell 300 to facilitate image capture regarding one or more nanowells in the image capture area 316. The positioning can include movement of the image capture area 316, or the flowcell 300, or both. For example, the emission optics can be relatively stationary in the analysis equipment, such that the image capture area 316 does not move during various scanning operations. For example, the flowcell 300 can be moved (e.g., by being positioned on a motorized stage that facilitates precise movement in at least one direction) relative to the image capture area 316 into one or more scanning positions. Here, an arrow 318 schematically illustrates that the flowcell 300 can be moved so that the image capture area 316 overlays at least some of the linear waveguides and the nanowells associated with them.

The light area 314 can remain stationary with, or be moved corresponding to, or be moved independently of, the image capture area 316. In this example, the light area 314 is aligned with all of the gratings 302 of the flowcell 300. Different incidence angles can be given to the illuminating light that impinges on the light area 314, in order to selectively couple light into at least one, but not at least one other, of the linear waveguides of the flowcell 300. For example, when scanning is done in the direction of the arrow 318, the incident angle can be chosen such that the gratings 302A and 302C (and others having similar grating periods) will couple the light impinging at the light area 314, whereas some other ones of the gratings (e.g., the grating 302B) will not couple the light impinging at the light area 314. Accordingly, illuminating light will be coupled into the linear waveguides 306A and 306C (and others whose gratings have similar grating periods), whereas the light will not be coupled into the linear waveguide 306B (and others whose gratings have similar grating periods). This can facilitate a selective illumination of the nanowells of the flowcell 300. For example, because the linear waveguides 306A and 306C have light coupled into them, excitation light can reach the nanowells 304A and 304C associated with the linear waveguide 306A, and a nanowell 304D associated with the linear waveguide 306C. On the other hand, excitation light should not reach the nanowell 304C because it is associated with the linear waveguide 306B which does not currently have light coupled into it. As such, the imaging can successfully proceed although some portions of the sample material (e.g., within the nanowells 304A and 304C) are positioned at the distance 310 from each other; that is, closer to each other than the resolution distance of the emission optics. During the scanning corresponding to the movement represented by the arrow 318 (which may be characterized as a line scan), only a particular subset of the linear waveguides can have light coupled into them. In some implementations, light is coupled into only every second linear waveguide. For example, light may be coupled into only the first, third, fifth, seventh, and so on, linear waveguide, whereas light is not coupled into the second, fourth, sixth, eighth, and so on, linear waveguide.

The scanning being illustrated in FIG. 3A can be described as the flowcell 300 being moved to the left in the image, and stopping at one or more selected positions corresponding to the linear waveguides as the image capture area 316 overlays them, until the flowcell 300 is to the left of the image capture area 316. One or more linear waveguides which do not have light coupled into them during the scan illustrated in FIG. 3A, and whose associated nanowells are accordingly not then subjected to excitation light, can be imaged in another scanning operation.

Such other scanning operation can be performed in the same direction as described above (e.g., along the direction of the arrow 318) or in another direction. FIG. 3B shows an example where scanning is done along a direction corresponding to an arrow 320, which direction is substantially, and in at least one instance completely, opposite to the direction associated with the arrow 318. The scanning being illustrated in FIG. 3B can be described as the flowcell 300 being moved to the right in the image, and stopping at one or more selected positions corresponding to the linear waveguides as the image capture area 316 overlays them, until the flowcell 300 is to the right of the image capture area 316. The positioning can include movement of the image capture area 316, or the flowcell 300, or both.

In this example, the light area 314 is aligned with all of the gratings 302 of the flowcell 300. Different incidence angles can be given to the illuminating light that impinges on the light area 314, in order to selectively couple light into at least one, but not at least one other, of the linear waveguides of the flowcell 300. For example, when scanning is done in the direction of the arrow 320, the incident angle can be chosen such that the grating 302B (and others having similar grating periods) will couple the light impinging at the light area 314, whereas some other ones of the gratings (e.g., the gratings 302A and 302C) will not couple the light impinging at the light area 314. Accordingly, illuminating light will be coupled into the linear waveguide 306B (and others whose gratings have similar grating periods), whereas the light will not be coupled into the linear waveguides 306A and 306C (and others whose gratings have similar grating periods). This can facilitate a selective illumination of the nanowells of the flowcell 300. For example, because the linear waveguide 306B has light coupled into it, excitation light can reach the nanowell 304C and others associated with the linear waveguide 306B. On the other hand, excitation light should not reach the nanowells 304A-304B that are associated with the linear waveguide 306A, or the nanowell 304D that is associated with the linear waveguide 306C, which linear waveguides do not currently have light coupled into them. As such, the imaging can successfully proceed although some portions of the sample material (e.g., within the nanowells 304A and 304C) are positioned at the distance 310 from each other; that is, closer to each other than the resolution distance of the emission optics. During the scanning corresponding to the movement represented by the arrow 320 (which may be characterized as a line scan), only a particular subset of the linear waveguides can have light coupled into them. In some implementations, light is coupled into only every second linear waveguide. For example, light may be coupled into only the second, fourth, sixth, eighth, and so on, linear waveguide, whereas light is not coupled into the first, third, fifth, seventh, and so on, linear waveguide.

In some implementations, two or more of the gratings 302 can instead or also have different refractive indices. For example, this can allow differential coupling regarding at least some of the linear waveguides 306A-306C.

Figure 4:
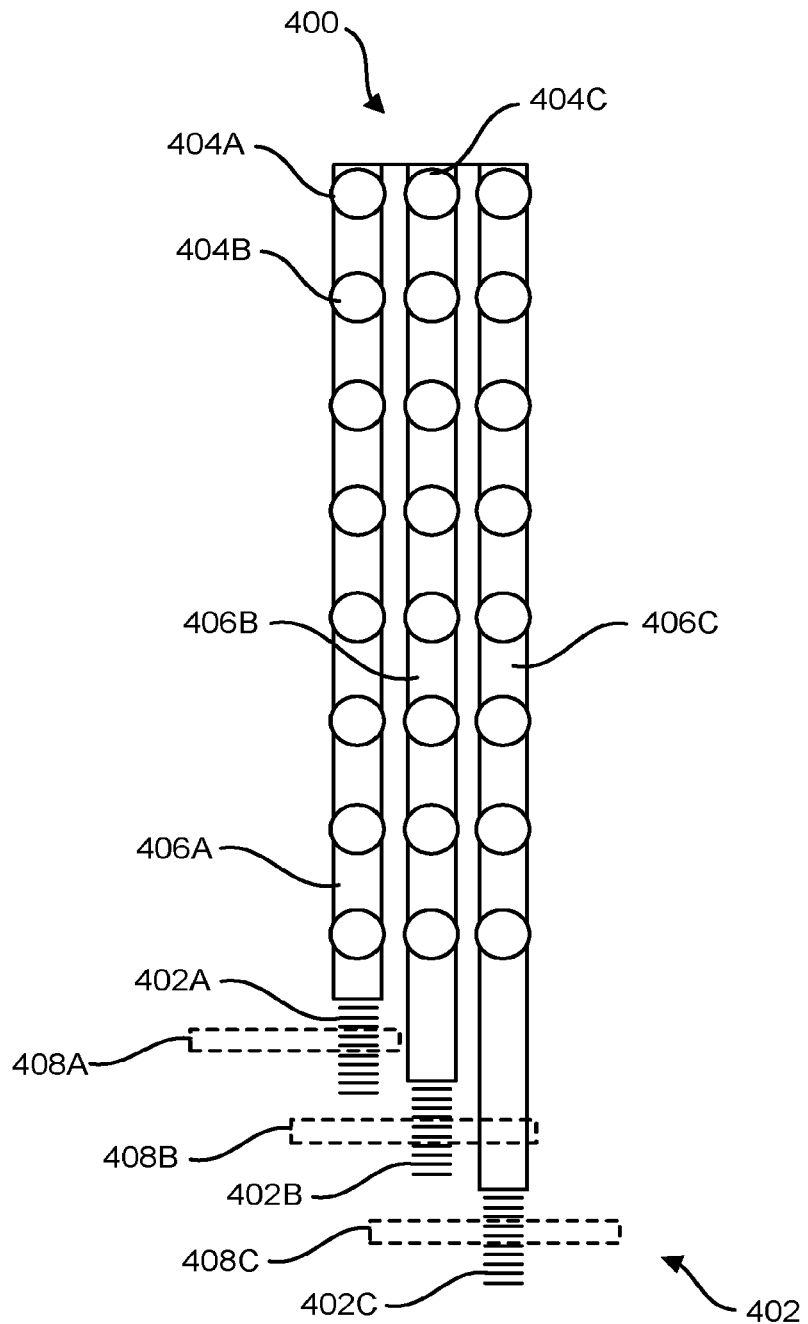
FIG. 4 shows another example of a flowcell having staggered gratings.

FIG. 4 shows another example of a flowcell 400 having staggered gratings 402. The flowcell 400 can be used with one or more methods described herein, and/or be used in combination with one or more systems or apparatuses described herein. Only a portion of the flowcell 400 is shown, for purposes of illustration.

The flowcell 400 includes nanowells, including a nanowell 404A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 404A is here associated with a linear waveguide 406A. In some implementations, the linear waveguides described with reference to the flowcell 4200 can be similar or identical to one or more other linear waveguides described herein. For example, the linear waveguide 406A is positioned adjacent (e.g., in contact with or near) the nanowell layer that includes the nanowell 404A.

Another nanowell 404B is also associated with the linear waveguide 406A. For example, the nanowell 404B is positioned adjacent to the nanowell 404A and both of the nanowells 404A-404B can interact with the linear waveguide 406A in an imaging process (e.g., by way of receiving electromagnetic radiation from the linear waveguide 406A). Another nanowell 404C, by contrast, is instead associated with a linear waveguide 406B. In some implementations, the linear waveguide 406B is positioned adjacent to the linear waveguide 406A. For example, cladding (not shown) and/or another material can be positioned between the linear waveguides 406A-406B.

The flowcell 400 can be used in one or more forms of imaging process. For example, sample material in the nanowells (including the nanowells 404A-404C) can be subjected to electromagnetic radiation from respective linear waveguides (including the linear waveguides 406A-406B, respectively). Emissions resulting from such exposure to electromagnetic radiation (an example of emissions being fluorescence from fluorophores) can be captured using equipment (e.g., one or more cameras and/or other imaging devices). Such equipment is sometimes referred to by way of the expression emission equipment or a similar term. For example, emission equipment can include one or more cameras or other image sensors and at least one lens or other emission optics. In some implementations, the diffraction limit can be at least partially attributable to one or more characteristics of the emission optics. For example, based on the emission optics used, a resolution distance can be defined, the resolution distance marking the shortest distance that can be resolved using the emission optics. That is, when resolving features that are spaced apart by the resolution distance, the imaging system can be said to be operating at its highest available level of resolution.

The gratings 402 serve for coupling electromagnetic radiation into and/or out of the linear waveguides of the flowcell 400. Here, the linear waveguide 406A has a grating 402A, the linear waveguide 406B has a grating 402B, and a linear waveguide 406C has a grating 402C. The gratings 402A-402C can have the same or different periodic structure. In some implementations, either or all of the gratings 402A-402C can include a periodic structure of ridges interspersed by another material. For example, ridges of the gratings 402A-402C can have a pitch of about 200-300 nm, to name just one example.

The gratings 402A-402C can have one or more characteristics that facilitate selective coupling of electromagnetic radiation into the corresponding linear waveguide 406A-406C. In some implementations, one or more of the gratings 402 is spatially offset from one or more others of the gratings 402. The offset can be in a direction that is parallel to the linear waveguides 406A-406C. For example, the distance between the grating 402B and the closest nanowell of the nanowells associated with the linear waveguide 406B is here greater than the distance between the grating 402A and the closest nanowell of the nanowells associated with the linear waveguide 406A. As another example, the distance between the grating 402C and the closest nanowell of the nanowells associated with the linear waveguide 406C is here greater than the distance between the grating 402A and the closest nanowell of the nanowells associated with the linear waveguide 406A, and also greater than the distance between the grating 402B and the closest nanowell of the nanowells associated with the linear waveguide 406B. The characteristic of the gratings 402A-402C being spatially offset from each other facilitates coupling of electromagnetic radiation (e.g., light) into one of the linear waveguides (e.g., the linear waveguide 406A) without coupling the electromagnetic radiation (e.g., light) into another of the linear waveguides (e.g., the linear waveguide 406B or 406C). That is, the grating 402C is spatially offset in the direction parallel to the linear waveguides 406A-406C from each of the gratings 402A-402B.

In some implementations, coupling into the gratings 402A-402C can also or instead be differentiated by a beam parameter other than location of the light beam (e.g., but not limited to, angle of incidence, divergence, mode profile, polarization, aspect ratio, diameter, wavelength, and combinations thereof). In some implementations, coupling into the gratings 402A-402C can also or instead be differentiated by a coupler parameter (e.g., but not limited to, grating period, refractive index, pitch, groove width, groove height, groove spacing, grating non-uniformity, groove orientation, groove curvature, overall shape of the coupler, and combinations thereof). In some implementations, coupling into the gratings 402A-402C can also or instead be differentiated by a waveguide parameter regarding one or more linear waveguides of the flowcell 400 (e.g., but not limited to, cross-sectional profile, refractive index difference, mode matching with the coupler and/or beam, and combinations thereof).

Light areas 408A-408C are here schematically illustrated as rectangles with dashed outlines. The light areas 408A-408C represents positions where light or other electromagnetic radiation is caused to impinge as part of an imaging process. In some implementations, illuminating light generated by a laser can be directed at one or more of the light areas 408A-408C in order to eventually be coupled into the corresponding linear waveguide. For example, the laser light can be selected so as to correspond to fluorescence properties of one or more fluorophores in the sample material. Light can be directed to the light area 408A to couple light into the linear waveguide 406A without coupling the light into the linear waveguides 406B-406C. Light can be directed to the light area 408B to couple light into the linear waveguide 406B without coupling the light into the linear waveguides 406A or 408-408C. Light can be directed to the light area 408C to couple light into the linear waveguide 406C without coupling the light into the linear waveguides 406A-406B.

The flowcell 400 can have other linear waveguides in addition to the linear waveguides 406A-406C, with corresponding gratings. Individual gratings of such other linear waveguides can have spatial offsets similar to the spatial offsets of one of the gratings 402A-402C, or can have different spatial offsets. For example, light may be coupled into only the first, fourth, seventh, tenth, and so on, linear waveguide, whereas light is not coupled into the second, third, fifth, sixth, eighth, ninth, eleventh, twelfth, and so on, linear waveguide. More generally, in any individual scanning operation (corresponding to the use of a particular light area, such as one of the light areas 408A-408C), the ordinals of the linear waveguides into which light is coupled can form an arithmetic series where the nth ordinal $a_n$ (n=1, 2, 3, . . . ) can be expressed as $a_n=a_1+d(n-1)$, where $a_1$ is the first ordinal and d is a positive integer. For example, with $a_1=1$ and d=3 one obtains that the linear waveguides into which light is coupled have the ordinals 1, 4, 7, 10, and so on, corresponding to the example mentioned above. As another example, with $a_1=1$ and d=4 one obtains that the linear waveguides into which light is coupled have the ordinals 1, 5, 9, 13, and so on.

The examples described above illustrate that the flowcell 400 includes a nanowell layer having first (e.g., the nanowells associated with the linear waveguide 406A) and second (e.g., the nanowells associated with the linear waveguide 406B) sets of nanowells to receive a sample. The flowcell 400 includes a first linear waveguide (e.g., the linear waveguide 406A) aligned with the first set of nanowells, and a second linear waveguide (e.g., the linear waveguide 406B) aligned with the second set of nanowells; and a first grating (e.g., the grating 402A) for the first linear waveguide, and a second grating (e.g., the grating 402B-402C) for the second linear waveguide. The first grating has a first characteristic (e.g., being spatially offset from the gratings 402B-402C) to facilitate coupling of first light into the first linear waveguide without coupling the first light into the second linear waveguide.

Figure 5:
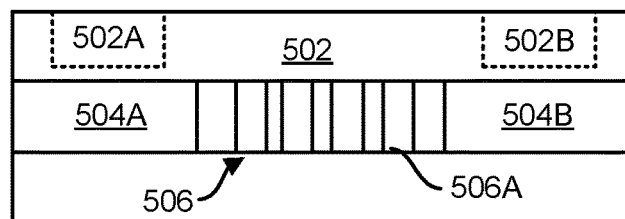
FIG. 5 shows a cross section of part of an example flowcell.

FIG. 5 shows a cross section of part of an example flowcell 500. The flowcell 500 can be used with one or more methods described herein, and/or be used in combination with one or more systems or apparatuses described herein. The flowcell 500 is shown in cross section, and only a portion of the flowcell 500 is shown, for purposes of illustration.

The flowcell 500 includes a nanowell layer 502 that includes nanowells 502A-502B. The nanowell layer 502 can be formed by nanoimprinting or a lift-off process. For example, the nanowells 502A-502B can be formed by application of a nano scale template to a resin.

The flowcell 500 includes linear waveguides 504A-504B. One or more of the linear waveguides 504A-504B can be aligned with one or more of the nanowells 502A-502B. For example, the linear waveguide 504A is here aligned with the nanowell 502A, and the linear waveguide 504B is here aligned with the nanowell 502B.

Each of the linear waveguides 504A-504B can have one or more gratings (omitted here for clarity) to couple electromagnetic radiation into and/or out of that linear waveguide 504A-504B. One or more directions of travel for the electromagnetic radiation in the linear waveguides 504A-504B can be employed. For example, the direction of travel can be into and/or out of the plane of the present illustration.

Each of the linear waveguides 504A-504B can be positioned against one or more types of cladding. The cladding can serve to constrain the electromagnetic radiation to the respective linear waveguide 504A-504B and prevent, or reduce the extent of, propagation of the radiation into other linear waveguides 504A-504B or other substrates (e.g., to reduce cross-coupling). Here, claddings 506 are shown as an example. In some implementations, the claddings 506 comprise a series of blocks. In some implementations, the claddings 506 provides refractive indices that alternate along the structure of the claddings 506. For example, a first one of the claddings 506 can have a first refractive index, a second one of the claddings 506 adjacent to the first one can have a second refractive index, a third one of the claddings 506 adjacent to the second one can have the first refractive index, and so on. The claddings 506 can be positioned against or near the linear waveguide 102A on different (e.g., opposing) sides thereof. For example, a cladding 506A can be positioned against or near the linear waveguide 504B. Here, the claddings 506 include multiple structures, including the cladding 506A. The claddings 506 can be made from one or more suitable materials that serve to separate the linear waveguides 504A-504B from each other. In some implementations, the claddings 506 can be made from a material having a lower refractive index than the refractive index/indices of the linear waveguides 504A-504B. In some implementations, one or more of the claddings 506 includes a polymer material. In some implementations, the multiple structures of the claddings 506 can be interspersed by regions of vacuum or another material (e.g., air or a liquid).

Figure 6:
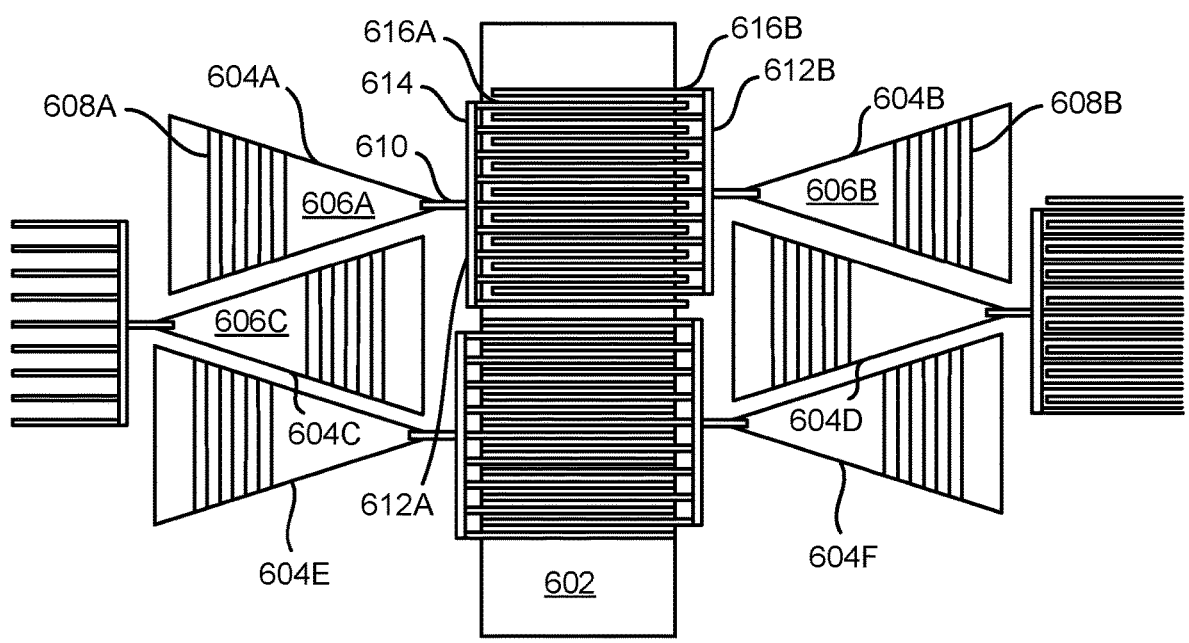
FIG. 6 shows an example of a flowcell where multiple linear waveguides share a common grating.

FIG. 6 shows an example of a flowcell 600 where multiple linear waveguides share a common grating. The flowcell 600 can be used with one or more methods described herein, and/or be used in combination with one or more systems or apparatuses described herein. The flowcell 500 is shown in a top view, and only a portion of the flowcell 600 is shown, for purposes of illustration.

The flowcell 600 includes a substrate 602. In some implementations, the substrate 602 serves as a base layer for the flowcell 600 and can support one or more layers and/or other structures. For example, the substrate 602 can support one or more linear waveguide components 604A and a nanowell layer (not shown).

The linear waveguide component 604A includes a coupling component 606A having a grating 608A. A linear waveguide connector 610 connects the coupling component 606A and a linear waveguide array 612A to each other. The linear waveguide array 612A includes a linear waveguide distributor 614 coupled to the linear waveguide connector 610, and multiple linear waveguides 616A arranged parallel to each other and being coupled to the linear waveguide distributor 614. In operation, light that is incident on the grating 608A can be coupled by the coupling component 606A and the linear waveguide connector 610 into the linear waveguide array 612A. In the linear waveguide array 612A the linear waveguide distributor 614 can distribute the light into the linear waveguides 616A. In some implementations, the linear waveguides 616A are positioned adjacent nanowells (not shown) to facilitate imaging as part of sample analysis. For example, rows of nanowells can be positioned along each of the linear waveguides 616A. The linear waveguide component 604A can be made from one or more suitable materials that facilitate propagation of electromagnetic radiation. In some implementations, the material(s) of the linear waveguide component 604A can include a polymer material. In some implementations, the material(s) of the linear waveguide component 604A can include $Ta_2O_5$ and/or $SiN_x$.

The linear waveguide array 612A can facilitate placement of one or more other components of the flowcell 600. In some implementations, the flowcell 600 includes a linear waveguide component 604B that is positioned on an opposite side of the substrate 602 from the linear waveguide array 612A. The linear waveguide component 604B can include a coupling component 606B coupled to a linear waveguide array 612B. In some implementations, individual linear waveguides 616B of the linear waveguide array 612B can be interspersed between the respective linear waveguides 616A of the linear waveguide array 612A. For example, two of the linear waveguides 616A can be positioned on respective opposing sides of one of the linear waveguides 616B. The two of the linear waveguides 616A are then sharing the same grating, in this example the grating 608A of the linear waveguide component 604A.

In some implementations, the linear waveguide 616A and the linear waveguide 616B can be positioned closer to each other than a resolution distance of emission optics. For example, during a first scanning stage light can be coupled into the linear waveguides 616A of the linear waveguide component 604A and not into the linear waveguides 616B of the linear waveguide component 604B. During a second scanning stage, moreover, light can instead be coupled into the linear waveguides 616B of the linear waveguide component 604B and not into the linear waveguides 616A of the linear waveguide component 604A.

At least one of the coupling components 606A-604B can include a substrate having an substantially, and in at least one instance completely, triangular shape. This can provide advantages in terms of efficient positioning of multiple flowcell. A linear waveguide component 604C may not be considered to be a part of the flowcell 600 but may instead be considered to be a part of another flowcell (not shown). In some implementations, the triangular substrate of the coupling component 606A, and a corresponding triangular substrate of a coupling component 606C of the linear waveguide component 604C can be positioned adjacent each other. For example, the coupling components 606A and 606C can be positioned in opposing orientations so as to provide an efficient packing of the linear waveguide components 604A and 604C next to each other.

The grating 608A can be positioned toward a first end of the linear waveguide component 604A (in this illustration, toward a left end thereof, for example). Moreover, a grating 608B can be positioned toward a second end of the linear waveguide component 604B (in this illustration, toward a right end thereof, for example). The first end can be positioned opposite from the second end in a direction parallel to rows of nanowells (e.g., the direction being parallel to the linear waveguides 616A-616B).

More or fewer linear waveguide components than shown can be used. In some implementations, respective linear waveguide components 604D-604F are implemented. For example, the linear waveguide components 604E-604F can be considered part of the flowcell 600, whereas the linear waveguide component 604D can be considered part of another flowcell (not shown) which is separate from the flowcell of the linear waveguide component 604C.

In some implementations, coupling into the grating 608A and/or others can be differentiated by a beam parameter (e.g., but not limited to, location of the light beam, angle of incidence, divergence, mode profile, polarization, aspect ratio, diameter, wavelength, and combinations thereof). In some implementations, coupling into the grating 608A and/or others can also or instead be differentiated by a coupler parameter (e.g., but not limited to, grating period, refractive index, pitch, groove width, groove height, groove spacing, grating non-uniformity, groove orientation, groove curvature, overall shape of the coupler, and combinations thereof). In some implementations, coupling into the grating 608A and/or others can also or instead be differentiated by a waveguide parameter regarding one or more linear waveguides of the flowcell 600 (e.g., but not limited to, cross-sectional profile, refractive index difference, mode matching with the coupler and/or beam, and combinations thereof).

Figure 7:
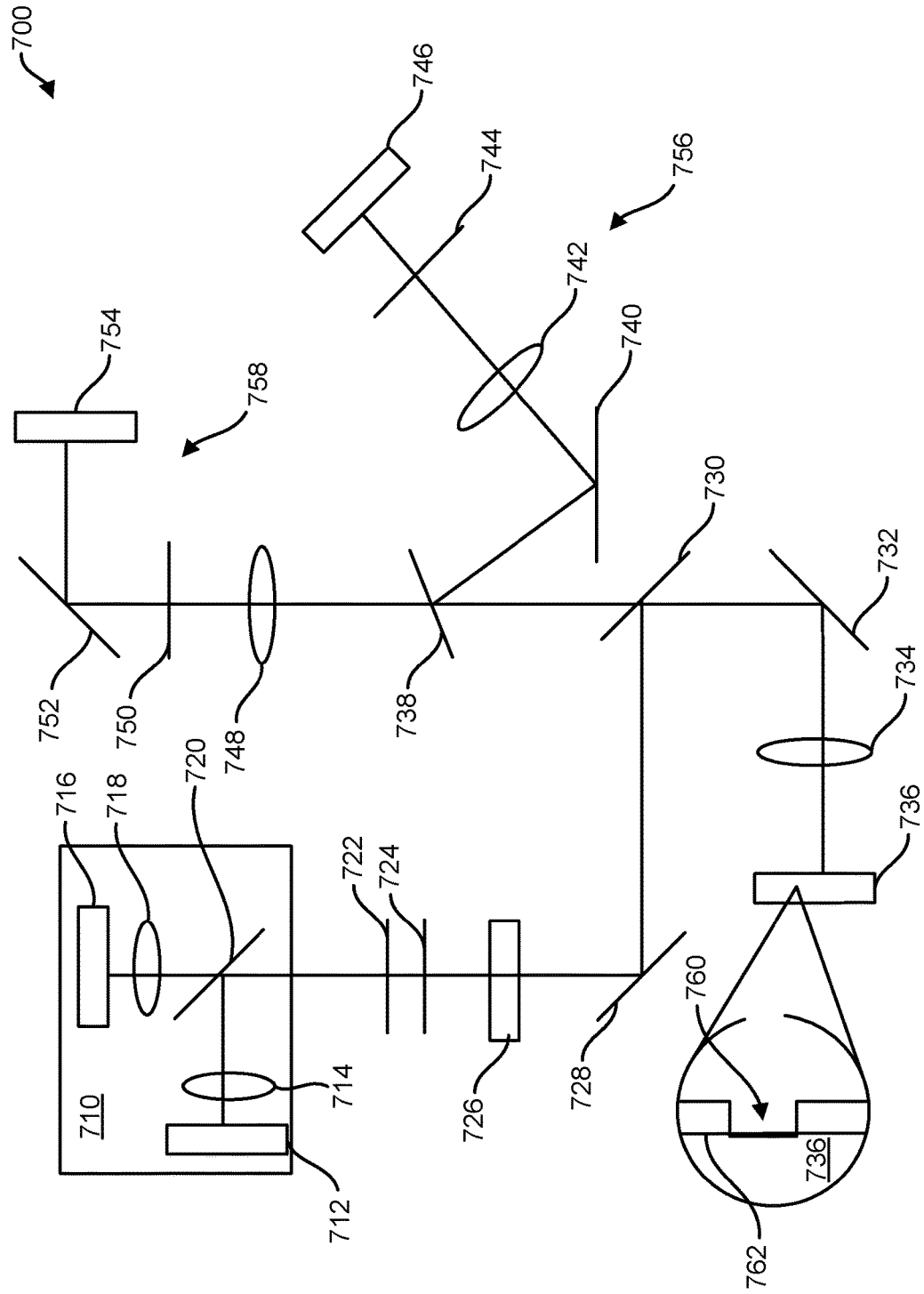
FIG. 7 is a diagram of an example illumination system.

FIG. 7 is a diagram of an example illumination system 700. The illumination system 700 can be used with one or more methods described herein, and/or be used in combination with one or more systems or apparatuses described herein.

The illumination system 700 includes a light source assembly 710, a mirror 728, an objective lens 734, a flowcell 736, an emission dichroic filter 738, a first optical detection subsystem 756, and a second optical detection subsystem 758. The illumination system 700 enables simultaneous imaging of two color channels. In some implementations, another illumination system can be configured to enable simultaneous imaging of more than two color channels, e.g., three color channels, four color channels, or more. It is noted that there may be other optical configurations that can produce a similar, simultaneous imaging of multiple color channels.

The light source assembly 710 produces excitation illumination that is incident on the flowcell 736. This excitation illumination in turn will produce emitted illumination, or fluoresced illumination, from one or more fluorescent dyes that will be collected using the lenses 742 and 748. The light source assembly 710 includes a first excitation illumination source 712 and corresponding converging lens 714, a second excitation illumination source 716 and corresponding converging lens 718, and a dichroic filter 720.

The first excitation illumination source 712 and the second excitation illumination source 716 illustrate an illumination system that can simultaneously provide respective excitation illumination lights for a sample (e.g., corresponding to respective color channels). In some implementations, each of the first excitation illumination source 712 and the second excitation illumination source 716 includes a light emitting diode (LED). In some implementations, at least one of the first excitation illumination source 712 and the second excitation illumination source 716 includes a laser. The converging lenses 714 and 718 are each set a distance from the respective excitation illumination sources 712 and 716 such that the illumination emerging from each of the converging lenses 714/718 is focused at a field aperture 722. The dichroic filter 720 reflects illumination from the first excitation illumination source 712 and transmits illumination from the second excitation illumination source 716.

In some implementations, the mixed excitation illumination output from the dichroic filter 720 can directly propagate toward the objective lens 134. In other implementations, the mixed excitation illumination can be further modified and/or controlled by additional intervening optical components prior to emission from the objective lens 734. The mixed excitation illumination can pass through a focus in the field aperture 722 to a filter 724 and then to a color-corrected collimating lens 726. The collimated excitation illumination from the lens 726 is incident upon a mirror 728 upon which it reflects and is incident on an excitation/emission dichroic filter 730. The excitation/emission dichroic filter 730 reflects the excitation illumination emitted from the light source assembly 710 while permitting emission illumination, which will be described further below, to pass through the excitation/emission dichroic filter 730 to be received by one or more optical subsystems 756, 758. The optical subsystems 756 and 758 exemplify a light collection system that can simultaneously collect multiplexed fluorescent light. The excitation illumination reflected from the excitation/emission dichroic filter 730 is then incident upon a mirror 732, from which it is incident upon the objective lens 134 towards the flowcell 736.

The objective lens 734 focuses the collimated excitation illumination from the mirror 732 onto the flowcell 136. In some implementations, the objective lens 734 is a microscope objective with a specified magnification factor of, for example, 1×, 2×, 4×, 5×, 6×, 8×, 10×, or higher. The objective lens 734 focuses the excitation illumination incident from the mirror 732 onto the flowcell 736 in a cone of angles, or numerical aperture, determined by the magnification factor. In some implementations, the objective lens 734 is movable on an axis that is normal to the flow cell (a "z-axis"). In some implementations, the illumination system 700 adjusts the z position of the tube lens 748 and tube lens 742 independently.

The flowcell 736 contains a sample, such as a nucleotide sequence or any other material, to be analyzed. The flowcell 736 can include one or more channels 760 (here schematically illustrated by way of a cross-section view in an enlargement) configured to hold sample material and to facilitate actions to be taken with regard to the sample material, including, but not limited to, triggering chemical reactions or adding or removing material. An object plane 762 of the objective lens 734, here schematically illustrated using a dashed line, extends through the flowcell 736. For example, the object plane 762 can be defined so as to be adjacent to the channel(s) 760.

The objective lens 734 can define a field of view. The field of view can define the area on the flowcell 736 from which an image detector captures emitted light using the objective lens 734. One or more image detectors, e.g., detectors 746 and 754, can be used. The illumination system 700 can include separate image detectors 746 and 754 for the respective wavelengths (or wavelength ranges) of the emitted light. At least one of the image detectors 746 and 754 can include a charge-coupled device (CCD), such as a time-delay integration CCD camera, or a sensor fabricated based on complementary metal-oxide semiconductor (CMOS) technology, such as chemically sensitive field effect transistors (chemFET), ion-sensitive field effect transistors (ISFET), and/or metal oxide semiconductor field effect transistors (MOSFET).

In some implementations, the illumination system 700 can include a structured illumination microscope (SIM). SIM imaging is based on spatially structured illumination light and reconstruction to result in a higher resolution image than an image produced solely using the magnification from the objective lens 734. For example, the structure can consist of or include a pattern or grating that interrupts the illuminating excitation light. In some implementations, the structure can include patterns of fringes. Fringes of light can be generated by impinging a light beam on a diffraction grating such that reflective or transmissive diffraction occurs. The structured light can be projected onto the sample, illuminating the sample according to the respective fringes which may occur according to some periodicity. To reconstruct an image using SIM, the two or more patterned images are used where the pattern of excitation illumination are at different phase angles to each other. For example, images of the sample can be acquired at different phases of the fringes in the structured light, sometimes referred to as the respective pattern phases of the images. This can allow various locations on the sample to be exposed to a multitude of illumination intensities. The set of resulting emitted light images can be combined to reconstruct the higher resolution image.

The sample material in the flowcell 736 is contacted with fluorescent dyes that couple to corresponding nucleotides. The fluorescent dyes emit fluorescent illumination upon being irradiated with corresponding excitation illumination incident on the flowcell 736 from the objective lens 734. The emitted illumination is identified with wavelength bands, each of which can be categorized to a respective color channel. The fluorescent dyes are chemically conjoined with respective nucleotides, e.g., containing respective nucleobases. In this way, a dNTP labeled with a fluorescent dye may be identified based upon an emitted light wavelength being within a corresponding wavelength band when detected by an image detector 746, 754.

The objective lens 734 captures fluorescent light emitted by the fluoresced dye molecules in the flow cell 736. Upon capturing this emitted light, the objective lens 734 collects and conveys collimated light. This emitted light then propagates back along the path in which the original, excitation illumination arrived from the light source assembly 710. It is noted that there is little to no interference expected between the emitted and excitation illumination along this path because of the lack of coherence between the emitted light and excitation illumination. That is, the emitted light is a result of a separate source, namely that of the fluorescent dye in contact with the sample material in the flowcell 736.

The emitted light, upon reflection by the mirror 732, is incident on the excitation/emission dichroic filter 730. The filter 730 transmits the emitted light to a dichroic filter 738.

In some implementations, a dichroic filter 738 transmits illumination associated with the blue color channel and reflects illumination associated with the green color channel. In some implementations, the dichroic filter 738 is selected such that the dichroic filter 738 reflects emitted illumination to an optical subsystem 756 that is within the defined green wavelength band and transmits emitted illumination to an optical subsystem 758 that is within the defined blue wavelength band, as discussed above. The optical subsystem 756 includes a tube lens 742, a filter 744, and the image detector 746. The optical subsystem 758 includes a tube lens 748, a filter 750, and the image detector 754.

In some implementations, the dichroic filter 738 and the dichroic filter 7120 operate similarly to each other (e.g., both may reflect light of one color and transmit light of another color). In other implementations, the dichroic filter 738 and the dichroic filter 720 operate differently from each other (e.g., the dichroic filter 738 may transmit light of a color that the dichroic filter 720 reflects, and vice versa).

In some implementations, the emitted illumination encounters a mirror 752 prior to the image detector 754. In example shown, the optical path in the optical subsystem 758 is angled so that the illumination system 700 as a whole may satisfy space or volume requirements. In some implementations, both such subsystems 756 and 758 have optical paths that are angled. In some implementations, neither of the optical paths in the subsystem 756 nor 758 is angled. As such, one or more of multiple optical subsystems can have at least one angled optical path.

Each tube lens 742 and 748 focuses the emitted illumination incident upon it onto respective image detectors 746 and 754. Each detector 746 and 754 includes, in some implementations, a CCD array. In some implementations, each image detector 746 and 754 includes a complementary metal-oxide semiconductor (CMOS) sensor.

The illumination system 700 is not required to be as shown in FIG. 7. For example, each of the mirrors 728, 732, 740 may be replaced with a prism or some other optical device that changes the direction of illumination. Each lens may be replaced with a diffraction grating, a diffractive optic, a Fresnel lens, or some other optical device that produces collimated or focused illumination from incident illumination.

Figure 8:
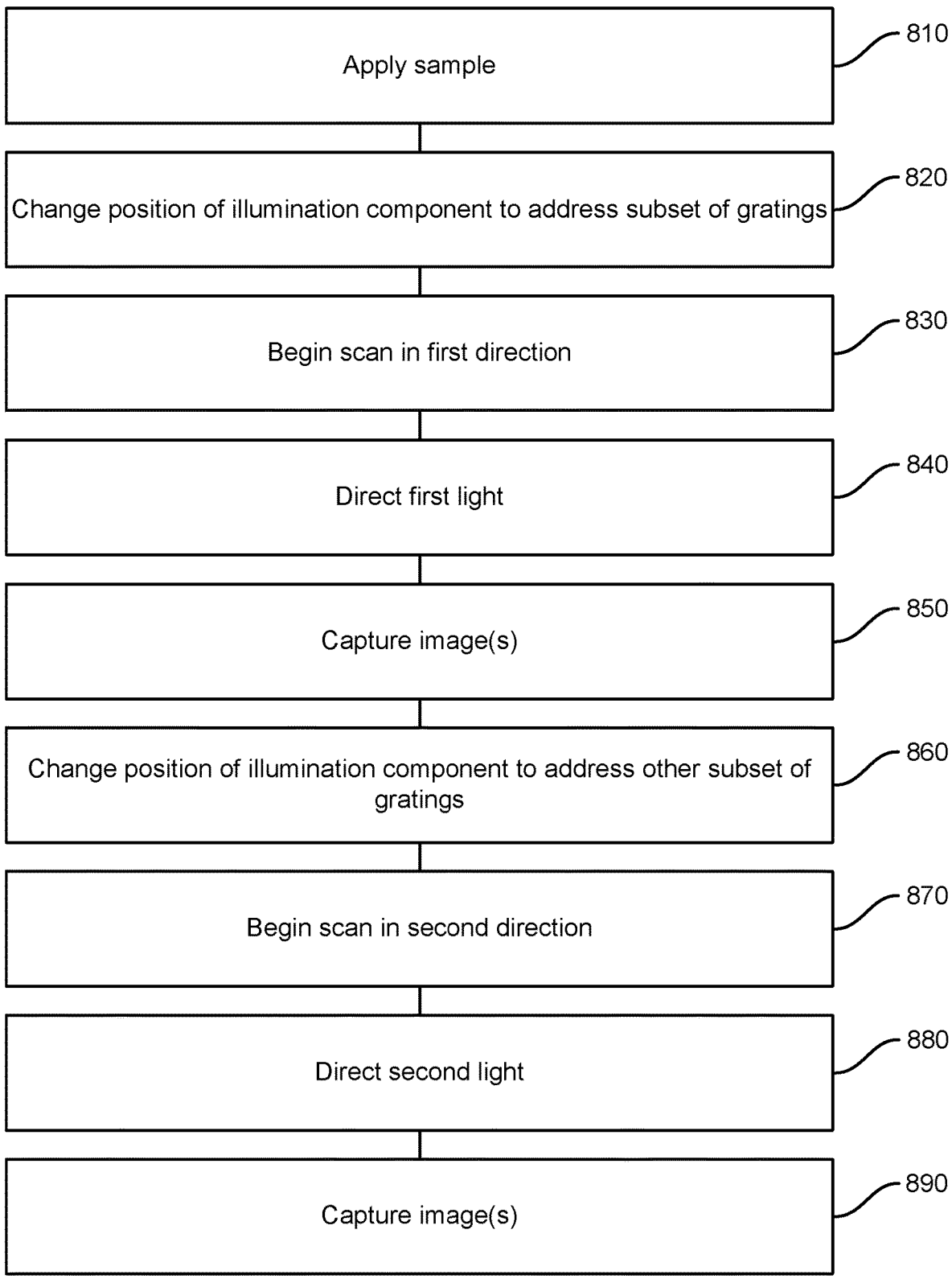
FIGS. 8-9 are flowcharts of example methods.
Figure 9:
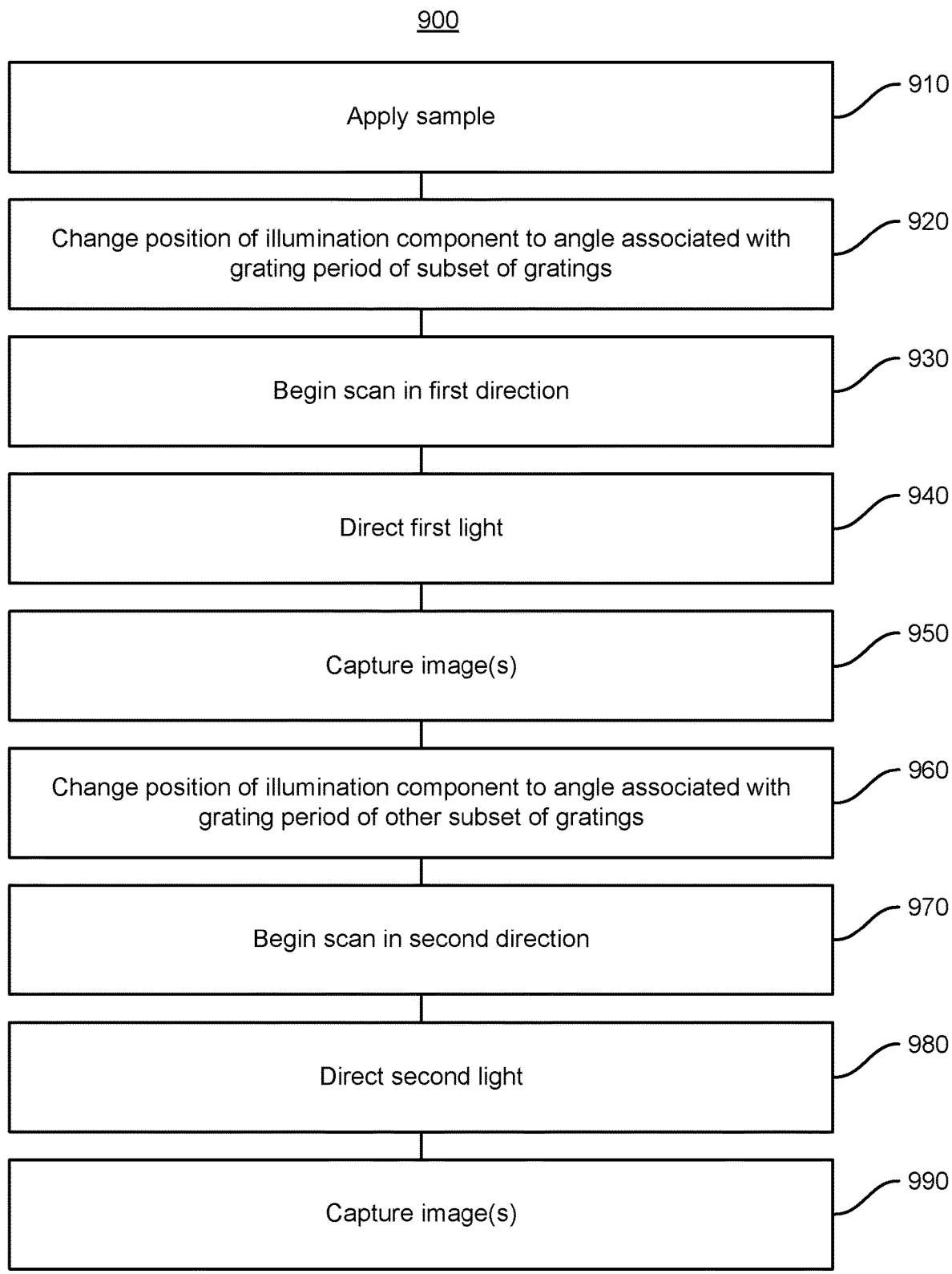

FIGS. 8-9 are flowcharts of example methods 800 and 900. The method 800 or 900, or both, can be performed using, and/or in combination with, one or more other examples described herein. More or fewer operations can be performed, and/or two or more operations can be performed in a different order, unless otherwise indicated.

At 810, a sample can be applied to first and second rows of nanowells of a flowcell. In some implementations, the sample can be applied to the rows of nanowells associated with the linear waveguides 206A-206B in FIG. 2A. In some implementations, the sample can be applied to the rows of nanowells associated with the linear waveguides 406A-406B in FIG. 4. For example, the sample can include genetic material.

At 820, a position of an illumination component can be changed to address a subset of gratings. In some implementations, the position of the illumination component is changed so that illuminating light will or does impinge on the light area 214 in FIG. 2A, when the light area 214 is aligned with the gratings 202A and 202C and some others, but not with the grating 202B and some others. In some implementations, the position of the illumination component is changed so that illuminating light will or does impinge on the light area 408A in FIG. 4, which is aligned with the grating 402A, but not with the gratings 402B-402C. For example, the mirror 732 in FIG. 7 can be adjusted to change the location where light is incident. In some implementations, the flowcell can be moved or adjusted in addition to, or in lieu of, moving the illumination equipment.

At 830, scanning can begin in a first direction. In some implementations, scanning is performed in the direction corresponding to the arrow 218 in FIG. 2A. The positioning can include movement of an image capture area (e.g., movement of image capture apparatus), or the flowcell, or both.

At 840, first light can be directed at a first grating of a first linear waveguide aligned with the first row of nanowells, without coupling the first light into a second linear waveguide aligned with the second row of nanowells. In some implementations, first light is directed at the light area 214 in FIG. 2A, when the light area 214 at least in part overlays the gratings 202A and 202C. Because the grating 202B is spatially offset from the gratings 202A and 202C, the first light is not coupled into the linear waveguide 206B. In some implementations, first light is directed at the light area 408A in FIG. 4 which at least in part overlays the grating 402A. Because the gratings 402B-402C are spatially offset from the grating 402A, the first light is not coupled into the linear waveguides 406B-406C.

At 850, one or more images can be captured. In some implementations, an image can be captured of the image capture area 216 in FIG. 2A when the image capture area 216 at least in part overlays some aspect of the flowcell 200. In a similar way, one or more images can be captured of the flowcell 400 in FIG. 4. For example, image capture can include a line scan.

At 860, a position of the illumination component can be changed to address another subset of gratings. In some implementations, the position of the illumination component is changed so that illuminating light will or does impinge on the light area 214 in FIG. 2B, when the light area 214 is aligned with the grating 202B and some others, but not with the gratings 202A and 202C and some others. In some implementations, the position of the illumination component is changed so that illuminating light will or does impinge on the light area 408B in FIG. 4, which is aligned with the grating 402B, but not with the gratings 402A or 402C. For example, the mirror 732 in FIG. 7 can be adjusted to change the location where light is incident. In some implementations, the flowcell can be moved or adjusted in addition to, or in lieu of, moving the illumination equipment.

At 870, scanning can begin in a second direction. The second direction can be the same as, or different from, the first direction. In some implementations, scanning is performed in the direction corresponding to the arrow 220 in FIG. 2B. The positioning can include movement of an image capture area (e.g., movement of image capture apparatus), or the flowcell, or both.

At 880, second light can be directed at a second grating of a second linear waveguide aligned with the second row of nanowells, without coupling the second light into the first linear waveguide. In some implementations, the second light is directed at the light area 214 in FIG. 2B, when the light area 214 at least in part overlays the grating 202B. Because the gratings 202A and 202C are spatially offset from the grating 202B, the second light is not coupled into the linear waveguides 206A or 206C. In some implementations, the second light is directed at the light area 408B in FIG. 4, when the light area 408B at least in part overlays the grating 402B. Because the gratings 402A and 402C are spatially offset from the grating 402B, the second light is not coupled into the linear waveguides 406A and 406C.

At 890, one or more images can be captured. In some implementations, an image can be captured of the image capture area 216 in FIG. 2B when the image capture area 216 at least in part overlays some aspect of the flowcell 200. In a similar way, one or more images can be captured of the flowcell 400 in FIG. 4. For example, image capture can include a line scan.

Turning now to the method 900 in FIG. 9, at 910 a sample can be applied to first and second rows of nanowells of a flowcell. In some implementations, the sample can be applied to the rows of nanowells associated with the linear waveguides 306A-306B in FIG. 3A. For example, the sample can include genetic material.

At 920, a position of an illumination component can be changed to an angle associated with a grating period of a subset of gratings. In some implementations, the position of the illumination component is changed so that illuminating light will or does have an incident angle at which the gratings 302A and 302C and some others couple light, but at which the grating 302B and some others do not couple light. For example, the mirror 732 in FIG. 7 can be adjusted to change the incident angle. In some implementations, the flowcell can be moved or adjusted in addition to, or in lieu of, adjusting the illumination equipment.

At 930, scanning can begin in a first direction. In some implementations, scanning is performed in the direction corresponding to the arrow 318 in FIG. 3A. The positioning can include movement of an image capture area (e.g., movement of image capture apparatus), or the flowcell, or both.

At 940, first light can be directed at a first grating of a first linear waveguide aligned with the first row of nanowells, without coupling the first light into a second linear waveguide aligned with the second row of nanowells. In some implementations, the first light is directed at the light area 314 in FIG. 3A when the light area 314 at least partially overlaps the gratings 302. Because the grating 302B has a different grating period than the gratings 302A and 302C, the first light is not coupled into the linear waveguide 306B.

At 950, one or more images can be captured. In some implementations, an image can be captured of the image capture area 316 in FIG. 3A when the image capture area 316 at least in part overlays some aspect of the flowcell 300.

At 960, a position of the illumination component can be changed to an angle associated with a grating period of another subset of gratings. In some implementations, the position of the illumination component is changed so that illuminating light will or does have an incident angle at which the grating 302B and some others couple light, but at which the gratings 302A and 302C and some others do not couple light. For example, the mirror 732 in FIG. 7 can be adjusted to change the location where light is incident. In some implementations, the flowcell can be moved or adjusted in addition to, or in lieu of, moving the illumination equipment.

At 970, scanning can begin in a second direction. The second direction can be the same as, or different from, the first direction. In some implementations, scanning is performed in the direction corresponding to the arrow 320 in FIG. 3B. The positioning can include movement of an image capture area (e.g., movement of image capture apparatus), or the flowcell, or both.

At 980, second light can be directed at a second grating of a second linear waveguide aligned with the second row of nanowells, without coupling the second light into the first linear waveguide. In some implementations, the second light is directed at the light area 314 in FIG. 3B, when the light area 314 at least partially overlaps the gratings 302. Because the gratings 302A and 302C have different grating periods than the grating 302B, the second light is not coupled into the linear waveguides 306A or 306C.

At 990, one or more images can be captured. In some implementations, an image can be captured of the image capture area 316 in FIG. 3B when the image capture area 316 at least in part overlays some aspect of the flowcell 300. For example, image capture can include a line scan.

Figure 10A:
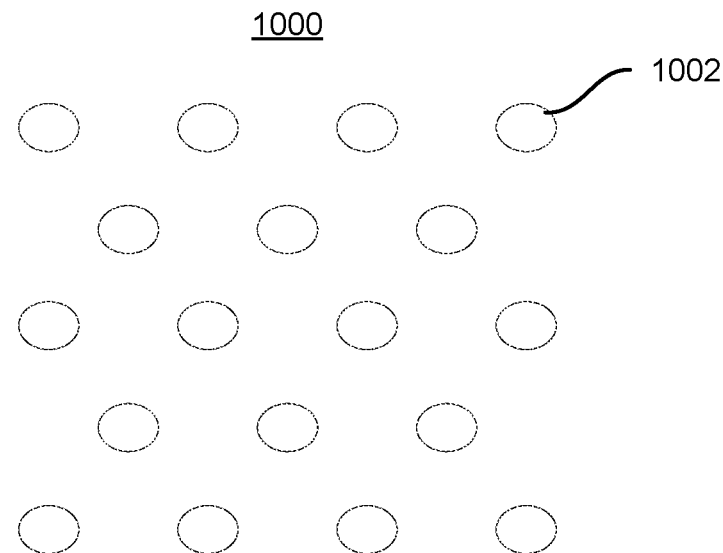
FIG. 10A shows an example of a hexagonal array of non-circular nanowells.

Some examples herein show nanowells having circular openings, for purposes of illustration only. In some implementations, non-circular nanowells can be used. FIG. 10A shows an example of a hexagonal array 1000 of non-circular nanowells 1002. The hexagonal array 1000 can be used with one or more methods described herein, and/or be used in combination with one or more systems or apparatuses described herein. For example, the hexagonal array 1000 can be used with circular nanowells or non-circular nanowells, or both. One or more of the non-circular nanowells 1002 can be used with one or more methods described herein, and/or be used in combination with one or more systems or apparatuses described herein. For example, the nanowells 1002 can be arranged in a hexagonal array or a non-hexagonal (e.g., otherwise polygonal) array, or both.

The size and/or shape of the non-circular nanowells 1002 can affect the imaging that is part of the analysis process. In some implementations, a fluorescence signal is collected from some or all of the non-circular nanowells 1002. The fluorescence signal can be affected by the size and/or shape of the non-circular nanowells 1002. For example, changes in the fluorescence signal(s) generated can affect the throughput of an analysis system (e.g., a sequencing system).

In some implementations, one or more of the non-circular nanowells 1002 has an elliptical opening. An ellipsis can be characterized by the respective lengths of the major and minor axes. The length of the minor axis can be expressed as a percentage of the major axis length, including, but not limited to, as having 5%, 15%, 35%, 65% or 95%, of the length of the major axis, to name just a few examples. Other geometries than elliptical of the non-circular nanowells are also possible.

Figure 10B:
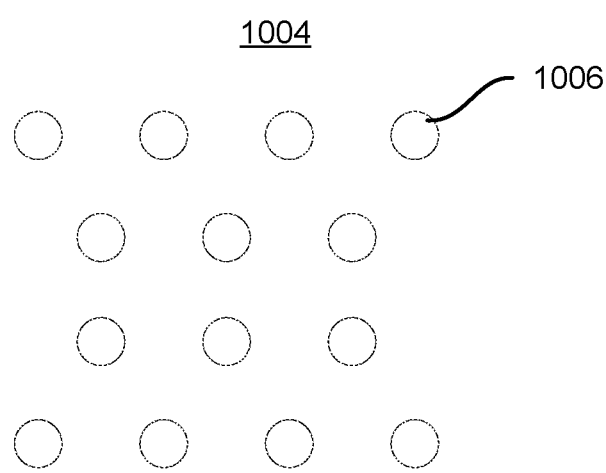
FIG. 10B shows an example of a triangular array of circular nanowells.

FIG. 10B shows an example of a triangular array 1004 of circular nanowells 1006. The triangular array 1004 can be used with one or more methods described herein, and/or be used in combination with one or more systems or apparatuses described herein. For example, the triangular array 1004 can be used with circular nanowells or non-circular nanowells, or both. One or more of the circular nanowells 1006 can be used with one or more methods described herein, and/or be used in combination with one or more systems or apparatuses described herein. For example, the circular nanowells 1006 can be arranged in a hexagonal array or a non-hexagonal (e.g., otherwise polygonal) array, or both.

Figure 11:
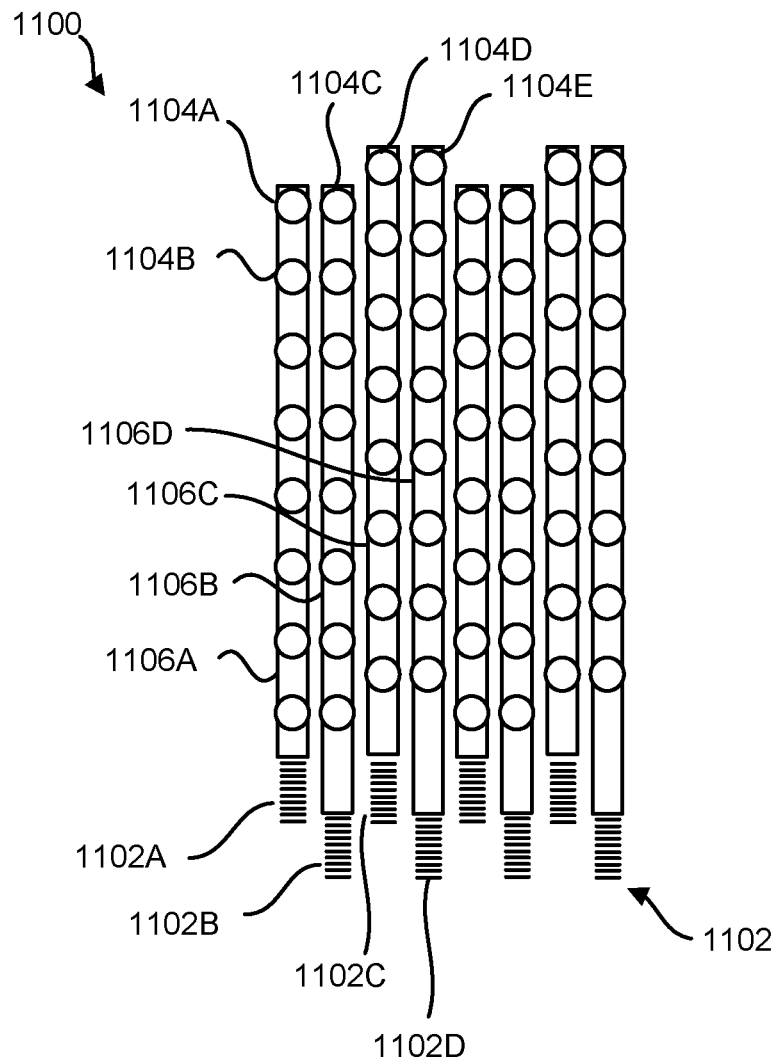
FIG. 11 shows another example of a flowcell having staggered gratings.

FIG. 11 shows another example of a flowcell 1100 having staggered gratings 1102. The flowcell 1100 can be used with one or more methods described herein, and/or be used in combination with one or more systems or apparatuses described herein. For example, the flowcell 1100 can be used with staggered gratings or non-staggered gratings, or both. One or more of the staggered gratings 1102 can be used with one or more methods described herein, and/or be used in combination with one or more systems or apparatuses described herein. For example, the staggered gratings 1102 can be used with nanowells arranged in a hexagonal array or a non-hexagonal (e.g., otherwise polygonal) array, or both.

The flowcell 1100 includes nanowells, including a nanowell 1104A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 1104A is here associated with a linear waveguide 1106A. In some implementations, the linear waveguides described with reference to the flowcell 1100 can be similar or identical to one or more other linear waveguides described herein. For example, the linear waveguide 1106A is positioned adjacent (e.g., in contact with or near) to the nanowell layer that includes the nanowell 1104A.

Another nanowell 1104B is also associated with the linear waveguide 1106A. For example, the nanowell 1104B is positioned adjacent to the nanowell 1104A and both of the nanowells 1104A-1104B can interact with the linear waveguide 1106A in an imaging process (e.g., by way of receiving electromagnetic radiation from the linear waveguide 1106A). Another nanowell 1104C, by contrast, is instead associated with a linear waveguide 1106B. In some implementations, the linear waveguide 1106B is positioned adjacent to the linear waveguide 1106A. For example, cladding (not shown) and/or another material can be positioned between the linear waveguides 1106A-1106B.

A nanowell 1104D is here associated with a linear waveguide 1106C. In some implementations, the linear waveguide 1106C is positioned adjacent to the linear waveguide 1106B. For example, cladding (not shown) and/or another material can be positioned between the linear waveguides 1106B-1106C.

A nanowell 1104E is here associated with a linear waveguide 1106D. In some implementations, the linear waveguide 1106D is positioned adjacent to the linear waveguide 1106C. For example, cladding (not shown) and/or another material can be positioned between the linear waveguides 1106C-1106D.

The nanowells 1104A-1104B and others here form a first set of nanowells (e.g., a row of nanowells) that extends along the linear waveguide 1106A. The nanowell 1104C and others here form a second set of nanowells (e.g., a row of nanowells) that extends along the linear waveguide 1106B. The nanowell 1104D and others here form a third set of nanowells (e.g., a row of nanowells) that extends along the linear waveguide 1106C. The nanowell 1104E and others here form a fourth set of nanowells (e.g., a row of nanowells) that extends along the linear waveguide 1106D. In some implementations, the first set of nanowells (e.g., the nanowells 1104A-1104B and others) is positioned so as to be in phase with the second set of nanowells (e.g., the nanowells 1104C and others). The first set of nanowells can be positioned at substantially, and in at least one instance completely, regular intervals along the linear waveguide 1106A. For example, each of the nanowells in the first set of nanowells at the linear waveguide 1106A has a corresponding nanowell in the second set of nanowells at the linear waveguide 1106B. The corresponding nanowell may be positioned directly across the cladding or another material between the linear waveguides 1106A-1106B from the nanowell.

Here, the nanowell 1104D and the others in the third set of nanowells are positioned at substantially, and in at least one instance completely, regular intervals along the linear waveguide 1106C. The third set of nanowells is positioned so as to be out of phase with at least the second set of nanowells. In some implementations, none of the nanowells in the second set of nanowells has a corresponding nanowell in the third set of nanowells directly across the cladding or other material. For example, each of the nanowells in the second set of nanowells may be equidistantly positioned between two adjacent ones of the nanowells in the third set of nanowells.

In some implementations, the fourth set of nanowells (e.g., the nanowell 1104E and others along the linear waveguide 1106D) is positioned so as to be in phase with the third set of nanowells (e.g., the nanowells 1104D and others along the linear waveguide 1106C). The fourth set of nanowells can be positioned at substantially, and in at least one instance completely, regular intervals along the linear waveguide 1106D. For example, each of the nanowells in the fourth set of nanowells at the linear waveguide 1106D has a corresponding nanowell in the third set of nanowells at the linear waveguide 1106C. The corresponding nanowell may be positioned directly across the cladding or another material between the linear waveguides 1106C-1106D from the nanowell.

The gratings 1102 serve for coupling electromagnetic radiation into and/or out of the linear waveguides of the flowcell 1100. Here, the linear waveguide 1106A has a grating 1102A, the linear waveguide 1106B has a grating 1102B, the linear waveguide 1106C has a grating 1102C, and the linear waveguide 1106D has a grating 1102D. Each of the gratings 1102A-1102D can have the same or different periodic structure. In some implementations, some or all of the gratings 1102A-1102D can include a periodic structure of ridges interspersed by another material. For example, ridges of the gratings 1102A-1102D can have a pitch of about 200-300 nm, to name just one example.

The gratings 1102A-1102D can have one or more characteristics that at least in part facilitate selective coupling of electromagnetic radiation into the corresponding linear waveguide 1106A-1106D. In some implementations, one or more of the gratings 1102 is spatially offset from one or more others of the gratings 1102. The offset can be in a direction that is parallel to the linear waveguides 1106A-1106D. For example, the distance between the grating 1102B and the closest nanowell of the nanowells associated with the linear waveguide 1106B is here greater than the distance between the grating 1102A and the closest nanowell of the nanowells associated with the linear waveguide 1106A. As another example, the distance between the grating 1102D and the closest nanowell of the nanowells associated with the linear waveguide 1106D is here greater than the distance between the grating 1102C and the closest nanowell of the nanowells associated with the linear waveguide 1106C. In some implementations, the gratings 1102A and 1102C have the same or a similar spatial offset. In some implementations, the gratings 1102B and 1102D have the same or a similar spatial offset. The characteristic of the gratings 1102A-1102D being spatially offset from each other at least in part facilitates coupling of electromagnetic radiation (e.g., light) into one of the linear waveguides (e.g., the linear waveguide 1106A and/or 1106C) without coupling the electromagnetic radiation (e.g., light) into another of the linear waveguides (e.g., the linear waveguide 1106B and/or 1106D).

In some implementations, coupling into the gratings 1102A-1102D can also or instead be differentiated by a beam parameter other than location of the light beam (e.g., but not limited to, angle of incidence, divergence, mode profile, polarization, aspect ratio, diameter, wavelength, and combinations thereof). In some implementations, coupling into the gratings 1102A-1102D can also or instead be differentiated by a coupler parameter (e.g., but not limited to, grating period, refractive index, pitch, groove width, groove height, groove spacing, grating non-uniformity, groove orientation, groove curvature, overall shape of the coupler, and combinations thereof). In some implementations, coupling into the gratings 1102A-1102D can also or instead be differentiated by a waveguide parameter regarding one or more of the linear waveguides 1106A-1106D (e.g., but not limited to, cross-sectional profile, refractive index difference, mode matching with the coupler and/or beam, and combinations thereof).

The examples described above illustrate that the flowcell 1100 includes a nanowell layer having first (e.g., the nanowells associated with the linear waveguide 1106A) and second (e.g., the nanowells associated with the linear waveguide 1106B) sets of nanowells to receive a sample. The flowcell 1100 includes a first linear waveguide (e.g., the linear waveguide 1106A) aligned with the first set of nanowells, and a second linear waveguide (e.g., the linear waveguide 1106B) aligned with the second set of nanowells; and a first grating (e.g., the grating 1102A) for the first linear waveguide, and a second grating (e.g., the grating 1102B) for the second linear waveguide. The first grating has a first characteristic (e.g., being spatially offset from the grating 1102B) to facilitate coupling of first light into the first linear waveguide without coupling the first light into the second linear waveguide.

Figure 12:
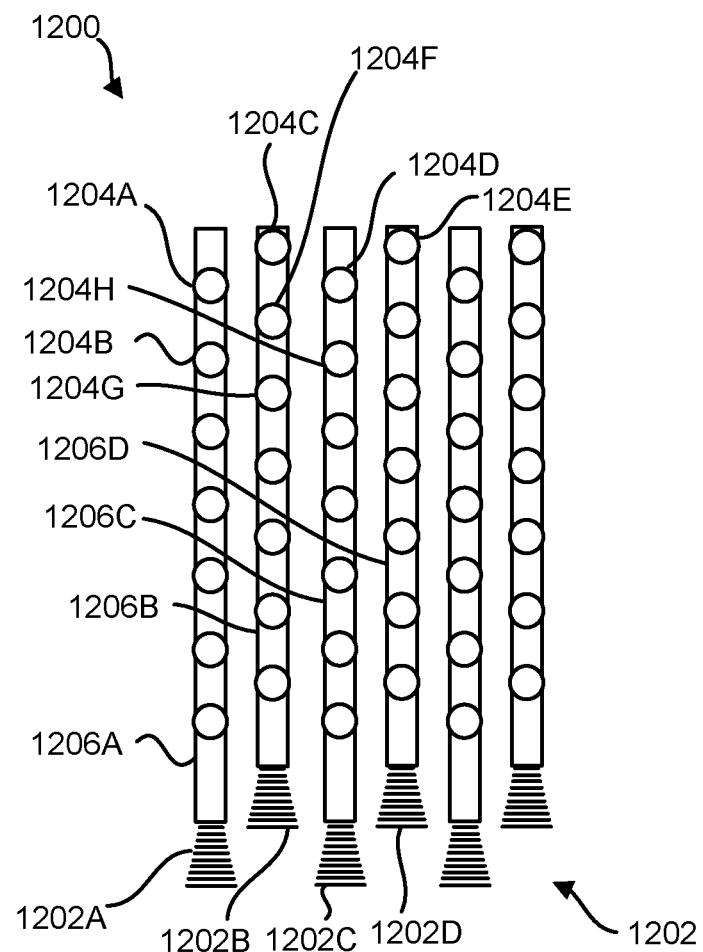
FIG. 12 shows another example of a flowcell having staggered gratings.

FIG. 12 shows another example of a flowcell 1200 having staggered gratings 1202. The flowcell 1200 can be used with one or more methods described herein, and/or be used in combination with one or more systems or apparatuses described herein. For example, the flowcell 1200 can be used with staggered gratings or non-staggered gratings, or both. One or more of the staggered gratings 1202 can be used with one or more methods described herein, and/or be used in combination with one or more systems or apparatuses described herein. For example, the staggered gratings 1202 can be used with nanowells arranged in a hexagonal array or a non-hexagonal (e.g., otherwise polygonal) array, or both.

The flowcell 1200 includes nanowells, including a nanowell 1204A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 1204A is here associated with a linear waveguide 1206A. In some implementations, the linear waveguides described with reference to the flowcell 1200 can be similar or identical to one or more other linear waveguides described herein. For example, the linear waveguide 1206A is positioned adjacent (e.g., in contact with or near) the nanowell layer that includes the nanowell 1204A.

Another nanowell 1204B is also associated with the linear waveguide 1206A. For example, the nanowell 1204B is positioned adjacent to the nanowell 1204A and both of the nanowells 1204A-1204B can interact with the linear waveguide 1206A in an imaging process (e.g., by way of receiving electromagnetic radiation from the linear waveguide 1206A). Another nanowell 1204C, by contrast, is instead associated with a linear waveguide 1206B. In some implementations, the linear waveguide 1206B is positioned adjacent to the linear waveguide 1206A. For example, cladding (not shown) and/or another material can be positioned between the linear waveguides 1206A-1206B.

A nanowell 1204D is here associated with a linear waveguide 1206C. In some implementations, the linear waveguide 1206C is positioned adjacent to the linear waveguide 1206B. For example, cladding (not shown) and/or another material can be positioned between the linear waveguides 1206B-1206C.

A nanowell 1204E is here associated with a linear waveguide 1206D. In some implementations, the linear waveguide 1206D is positioned adjacent to the linear waveguide 1206C. For example, cladding (not shown) and/or another material can be positioned between the linear waveguides 1206C-1206D.

The nanowells 1204A-1204B and others here form a first set of nanowells (e.g., a row of nanowells) that extends along the linear waveguide 1206A. The nanowell 1204C and others here form a second set of nanowells (e.g., a row of nanowells) that extends along the linear waveguide 1206B. The nanowell 1204D and others here form a third set of nanowells (e.g., a row of nanowells) that extends along the linear waveguide 1206C. The nanowell 1204E and others here form a fourth set of nanowells (e.g., a row of nanowells) that extends along the linear waveguide 1206D. In some implementations, the first set of nanowells (e.g., the nanowells 1204A-1204B and others) is positioned so as to be out of phase with the second set of nanowells (e.g., the nanowells 1204C and others). In some implementations, none of the nanowells in the first set of nanowells has a corresponding nanowell in the second set of nanowells directly across the cladding or other material. For example, each of the nanowells in the first set of nanowells may be equidistantly positioned between two adjacent ones of the nanowells in the second set of nanowells.

Here, the nanowell 1204D and the others in the third set of nanowells are positioned at substantially, and in at least one instance completely, regular intervals along the linear waveguide 1206C. The third set of nanowells is positioned so as to be out of phase with at least the second set of nanowells. In some implementations, none of the nanowells in the third set of nanowells has a corresponding nanowell in the second set of nanowells directly across the cladding or other material. For example, each of the nanowells in the third set of nanowells may be equidistantly positioned between two adjacent ones of the nanowells in the second set of nanowells. The third set of nanowells can be positioned so as to be in phase with at least the first set of nanowells.

In some implementations, the fourth set of nanowells (e.g., the nanowell 1204E and others along the linear waveguide 1206D) is positioned so as to be out of phase with the third set of nanowells (e.g., the nanowells 1204D and others along the linear waveguide 1206C). In some implementations, none of the nanowells in the fourth set of nanowells has a corresponding nanowell in the third set of nanowells directly across the cladding or other material. For example, each of the nanowells in the fourth set of nanowells may be equidistantly positioned between two adjacent ones of the nanowells in the third set of nanowells.

The gratings 1202 serve for coupling electromagnetic radiation into and/or out of the linear waveguides of the flowcell 1200. Here, the linear waveguide 1206A has a grating 1202A, the linear waveguide 1206B has a grating 1202B, the linear waveguide 1206C has a grating 1202C, and the linear waveguide 1206D has a grating 1202D. Each of the gratings 1202A1202D can have the same or different periodic structure. In some implementations, some or all of the gratings 1202A-1202D can include a periodic structure of ridges interspersed by another material. For example, ridges of the gratings 1202A-1202D can have a pitch of about 200-300 nm, to name just one example. The gratings 1202A-1202D can have one or more of multiple suitable shapes. In some implementations, the gratings 1202A-1202D have a truncated triangular shape.

The gratings 1202A-1202D can have one or more characteristics that at least in part facilitate selective coupling of electromagnetic radiation into the corresponding linear waveguide 1206A-1206D. In some implementations, one or more of the gratings 1202 is spatially offset from one or more others of the gratings 1202. The offset can be in a direction that is parallel to the linear waveguides 1206A-1206D. For example, the distance between the grating 1202B and the other end of the linear waveguide 1206B is here shorter than the distance between the grating 1202A and the other end of the linear waveguide 1206A. As another example, the distance between the grating 1202D and the other end of the linear waveguide 1206D is here shorter than the distance between the grating 1202C and the other end of the linear waveguide 1206C. In some implementations, the gratings 1202A and 1202C have the same or a similar spatial offset. In some implementations, the gratings 1202B and 1202D have the same or a similar spatial offset. The characteristic of the gratings 1202A-1202D being spatially offset from each other at least in part facilitates coupling of electromagnetic radiation (e.g., light) into one of the linear waveguides (e.g., the linear waveguide 1206A and/or 1206C) without coupling the electromagnetic radiation (e.g., light) into another of the linear waveguides (e.g., the linear waveguide 1206B and/or 1206D).

In some implementations, coupling into the gratings 1202A-1202D can also or instead be differentiated by a beam parameter other than location of the light beam (e.g., but not limited to, angle of incidence, divergence, mode profile, polarization, aspect ratio, diameter, wavelength, and combinations thereof). In some implementations, coupling into the gratings 1202A-1202D can also or instead be differentiated by a coupler parameter (e.g., but not limited to, grating period, refractive index, pitch, groove width, groove height, groove spacing, grating non-uniformity, groove orientation, groove curvature, overall shape of the coupler, and combinations thereof). In some implementations, coupling into the gratings 1202A-1202D can also or instead be differentiated by a waveguide parameter regarding one or more of the linear waveguides 1206A-1206D (e.g., but not limited to, cross-sectional profile, refractive index difference, mode matching with the coupler and/or beam, and combinations thereof).

The flowcell 1200 can have the nanowells arranged in any of multiple patterns. In the present example, the nanowells are arranged in a hexagonal array. A hexagonal array forms one or more hexagons. Here, the linear waveguide 1206B further includes nanowells 1204F-1204G, and the linear waveguide 1206C further includes a nanowell 1204H. The nanowells 1204A1204H are here positioned in form of a hexagon. The nanowells 1204A-1204B are here part of the first set of nanowells and are associated with the linear waveguide 1206A; the nanowells 1204C and 1204F-1204G are part of the second set of nanowells and are associated with the linear waveguide 1206B; the nanowells 1204D and 1204H are part of the third set of nanowells and are associated with the linear waveguide 1206C.

The examples described above illustrate that the flowcell 1200 includes a nanowell layer having first (e.g., the nanowells associated with the linear waveguide 1206A) and second (e.g., the nanowells associated with the linear waveguide 1206B) sets of nanowells to receive a sample. The flowcell 1200 includes a first linear waveguide (e.g., the linear waveguide 1206A) aligned with the first set of nanowells, and a second linear waveguide (e.g., the linear waveguide 1206B) aligned with the second set of nanowells; and a first grating (e.g., the grating 1202A) for the first linear waveguide, and a second grating (e.g., the grating 1202B) for the second linear waveguide. The first grating has a first characteristic (e.g., being spatially offset from the grating 1202B) to facilitate coupling of first light into the first linear waveguide without coupling the first light into the second linear waveguide.

Figure 13:
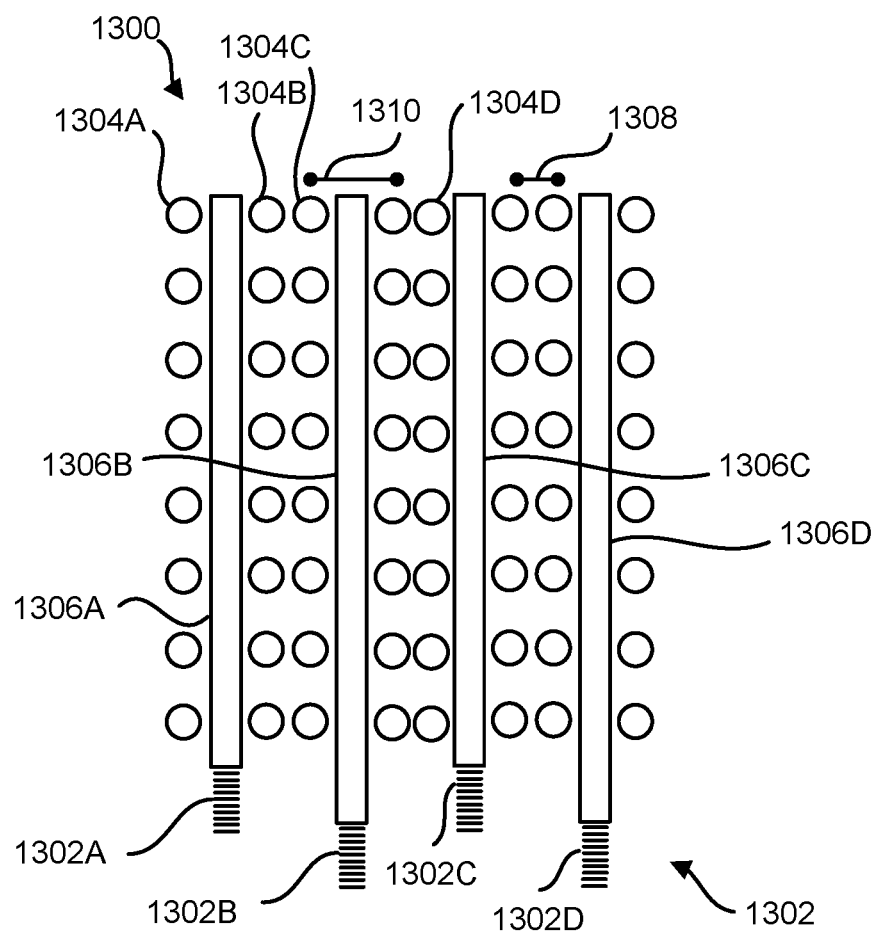
FIG. 13 shows another example of a flowcell having staggered gratings.

FIG. 13 shows another example of a flowcell 1300 having staggered gratings 1302. The flowcell 1300 can be used with one or more methods described herein, and/or be used in combination with one or more systems or apparatuses described herein. For example, the flowcell 1300 can be used with staggered gratings or non-staggered gratings, or both. One or more of the staggered gratings 1302 can be used with one or more methods described herein, and/or be used in combination with one or more systems or apparatuses described herein. For example, the staggered gratings 1302 can be used with nanowells arranged in a hexagonal array or a non-hexagonal (e.g., otherwise polygonal) array, or both.

The flowcell 1300 includes nanowells, including a nanowell 1304A, that are here illustrated using circular shapes. Only some of the nanowells will be specifically mentioned, and the other nanowells may be similar or identical to the one(s) discussed. The nanowells may be formed in a nanowell layer (e.g., by way of nanoimprinting or a lift-off process). For example, the nanowells can be formed in a resin using a nanoscale template. The nanowell layer is not explicitly shown in this example, for purposes of clarity. The nanowell 1304A is here associated with a linear waveguide 1306A. In some implementations, the linear waveguides described with reference to the flowcell 1300 can be similar or identical to one or more other linear waveguides described herein. For example, the linear waveguide 1306A is positioned adjacent (e.g., in contact with or near) to the nanowell layer that includes the nanowell 1304A. The nanowell 1304A is part of a first set of nanowells (e.g., one or more rows of nanowells) for the linear waveguide 1306A. Here, the row of nanowells of which the nanowell 1304A is part extends along the linear waveguide 1306A on one side thereof. For example, the row of nanowells does not overlap the linear waveguide 1306A in the shown perspective of the flowcell 1300.

Another nanowell 1304B is also associated with the linear waveguide 1306A. Like the nanowell 1304A, the nanowell 1304B is also part of the first set of nanowells (e.g., one or more rows of nanowells) for the linear waveguide 1306A. Here, the row of nanowells of which the nanowell 1304B is part extends along the linear waveguide 1306A on another side thereof. For example, the row of nanowells does not overlap the linear waveguide 1306A in the shown perspective of the flowcell 1300 and is positioned on an opposite side of the linear waveguide 1306A from the row of the nanowell 1304A. Both of the nanowells 1304A-1304B can interact with the linear waveguide 1306A in an imaging process (e.g., by way of receiving electromagnetic radiation from the linear waveguide 1306A).

Another nanowell 1304C is associated with a linear waveguide 1306B. In some implementations, the linear waveguide 1306B is parallel to and positioned adjacent to the linear waveguide 1306A. For example, cladding (not shown) and/or another material can be positioned between the linear waveguides 1306A-1306B. The nanowell 1304C is part of a second set of nanowells (e.g., one or more rows of nanowells) for the linear waveguide 1306B. Here, the row of nanowells of which the nanowell 1304C is part extends along the linear waveguide 1306B on one side thereof. For example, the row of nanowells does not overlap the linear waveguide 1306B in the shown perspective of the flowcell 1300. Another row of nanowells that is also part of the second set of nanowells can be positioned on the opposite side of the linear waveguide 1306B from the row of the nanowell 1304C.

Another nanowell 1304D is associated with a linear waveguide 1306C. In some implementations, the linear waveguide 1306C is parallel to and positioned adjacent to the linear waveguide 1306B. For example, cladding (not shown) and/or another material can be positioned between the linear waveguides 1306B-1306C. The nanowell 1304D is part of a third set of nanowells (e.g., one or more rows of nanowells) for the linear waveguide 1306C. Here, the row of nanowells of which the nanowell 1304D is part extends along the linear waveguide 1306C on one side thereof. For example, the row of nanowells does not overlap the linear waveguide 1306C in the shown perspective of the flowcell 1300. Another row of nanowells that is also part of the third set of nanowells can be positioned on the opposite side of the linear waveguide 1306C from the row of the nanowell 1304D.

Having nanowells positioned with offsets from the associated linear waveguide (e.g., as in the flowcell 1300) can provide one or more advantages. In some implementations, cross-talk between waveguides can be reduced or minimized. For example, this benefit can outweigh a somewhat lower packing density of the nanowells.

In some implementations, the nanowells in the rows of the first set of nanowells (e.g., the nanowells 1304A-1304B and others) are positioned so as to be in phase with each other. The nanowells in the nanowell rows on either side of the linear waveguide 1306A can be positioned at substantially, and in at least one instance completely, regular intervals along the linear waveguide 1306A. For example, each of the nanowells in one of these rows has a corresponding nanowell in the other row. The corresponding nanowell of the first set of nanowells may be positioned directly across the linear waveguides 1306A from the other nanowell of the first set of nanowells.

In some implementations, the first set of nanowells (e.g., the nanowells 1304A-1304B and others) are positioned so as to be in phase with nanowells of the second set of nanowells (e.g., the nanowell 1304C and others). The nanowells in the nanowell rows on either side of the linear waveguide 1306B can be positioned at substantially, and in at least one instance completely, regular intervals along the linear waveguide 1306B. For example, each of the nanowells in at least one of these rows has a corresponding nanowell in at least one of the rows of the first set of nanowells. The corresponding nanowell of the first set of nanowells may be positioned directly across the cladding or other material from the nanowell of the second set of nanowells.

The gratings 1302 serve for coupling electromagnetic radiation into and/or out of the linear waveguides of the flowcell 1300. Here, the linear waveguide 1306A has a grating 1302A, the linear waveguide 1306B has a grating 1302B, the linear waveguide 1306C has a grating 1302C, and a linear waveguide 1306D has a grating 1302D. Each of the gratings 1302A-1302D can have the same or different periodic structure. In some implementations, some or all of the gratings 1302A-1302D can include a periodic structure of ridges interspersed by another material. For example, ridges of the gratings 1302A-1302D can have a pitch of about 200-300 nm, to name just one example.

The gratings 1302A-1302D can have one or more characteristics that at least in part facilitate selective coupling of electromagnetic radiation into the corresponding linear waveguide 1306A-1306D. In some implementations, one or more of the gratings 1302 is spatially offset from one or more others of the gratings 1302. The offset can be in a direction that is parallel to the linear waveguides 1306A-1306D. For example, the distance between the grating 1302B and the closest nanowell of the nanowells associated with the linear waveguide 1306B is here greater than the distance between the grating 1302A and the closest nanowell of the nanowells associated with the linear waveguide 1306A. As another example, the distance between the grating 1302D and the closest nanowell of the nanowells associated with the linear waveguide 1306D is here greater than the distance between the grating 1302C and the closest nanowell of the nanowells associated with the linear waveguide 1306C. In some implementations, the gratings 1302A and 1302C have the same or a similar spatial offset. In some implementations, the gratings 1302B and 1302D have the same or a similar spatial offset. The characteristic of the gratings 1302A-1302D being spatially offset from each other at least in part facilitates coupling of electromagnetic radiation (e.g., light) into one of the linear waveguides (e.g., the linear waveguide 1306A and/or 1306C) without coupling the electromagnetic radiation (e.g., light) into another of the linear waveguides (e.g., the linear waveguide 1306B and/or 1306D).

Here, a distance 1308 is less than the resolution distance of the emission optics, and a distance 1310 is greater than, or about equal to, the resolution distance of the emission optics. The distance 1308 here represents the separation between the nearest nanowells associated with adjacent linear waveguides. The distance 1310 here represents a distance between nanowells associated with the same linear waveguide.

In some implementations, coupling into the gratings 1302A-1302D can also or instead be differentiated by a beam parameter other than location of the light beam (e.g., but not limited to, angle of incidence, divergence, mode profile, polarization, aspect ratio, diameter, wavelength, and combinations thereof). In some implementations, coupling into the gratings 1302A-1302D can also or instead be differentiated by a coupler parameter (e.g., but not limited to, grating period, refractive index, pitch, groove width, groove height, groove spacing, grating non-uniformity, groove orientation, groove curvature, overall shape of the coupler, and combinations thereof). In some implementations, coupling into the gratings 1302A-1302D can also or instead be differentiated by a waveguide parameter regarding one or more of the linear waveguides 1306A-1306D (e.g., but not limited to, cross-sectional profile, refractive index difference, mode matching with the coupler and/or beam, and combinations thereof).

Examples herein illustrate differential coupling of light into two or more linear waveguides. Differential coupling can be based on one or more parameters that characterize the analysis system, the parameter(s) having an effect on the extent to which light is (or is not) coupled into one or more linear waveguides. In some implementations, one or more such parameters can relate to the light beam that is the source of illumination (e.g., excitation illumination) for the analysis. For example, a coupler (e.g., a grating) may be relatively sensitive to one or more parameters, so a relatively minor change in the parameter(s) can facilitate differential coupling.

The examples described above illustrate that the flowcell 1300 includes a nanowell layer having first (e.g., the nanowells associated with the linear waveguide 1306A) and second (e.g., the nanowells associated with the linear waveguide 1306B) sets of nanowells to receive a sample. The flowcell 1300 includes a first linear waveguide (e.g., the linear waveguide 1306A) aligned with the first set of nanowells, and a second linear waveguide (e.g., the linear waveguide 1306B) aligned with the second set of nanowells; and a first grating (e.g., the grating 1302A) for the first linear waveguide, and a second grating (e.g., the grating 1302B) for the second linear waveguide. The first grating has a first characteristic (e.g., being spatially offset from the grating 1302B) to facilitate coupling of first light into the first linear waveguide without coupling the first light into the second linear waveguide.

Figure 14:
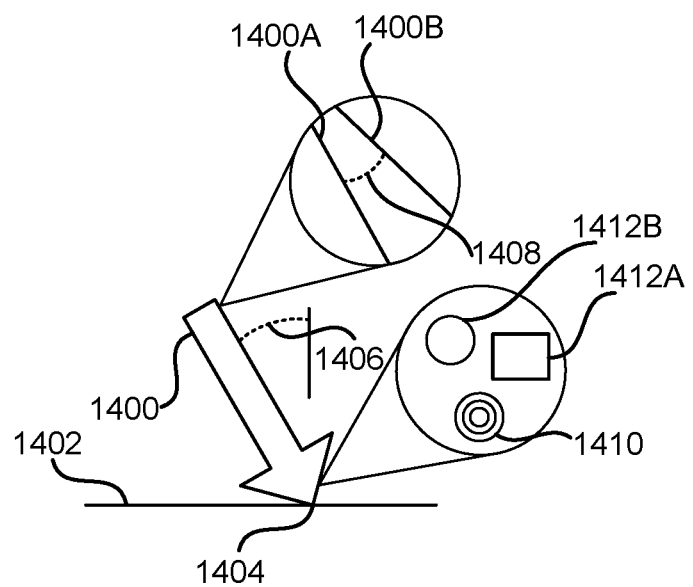
FIG. 14 schematically shows a light beam impinging on a surface.

FIG. 14 schematically shows a light beam 1400 impinging on a surface 1402. Examples and/or concepts described with reference to the light beam 1400 can be taken into account and/or employed in connection with one or more methods described herein, and/or be used in combination with one or more systems or apparatuses described herein.

The light beam 1400 is here incident at a location 1404 of the surface 1402. In some implementations, the location 1404 is a beam parameter that can be selected and/or adjusted to facilitate differential coupling. For example, the location 1404 where the light beam 1400 impinges can affect the extent to which light is (or is not) coupled into one or more linear waveguides.

One or more angles can characterize the incidence of the light beam 1400. Here, the light beam 1400 has an angle of incidence 1406 with respect to a normal of the surface 1402. In some implementations, the angle of incidence 1406 is a beam parameter that can be selected and/or adjusted to facilitate differential coupling. For example, the angle of incidence 1406 of the light beam 1400 can affect the extent to which light is (or is not) coupled into one or more linear waveguides.

One or more characteristics of the light beam 1400 can be taken into account. Here, the light beam 1400 includes individual light rays 1400A-1400B that are not parallel to each other but rather form an angle 1408 that is a nonzero angle. A divergence of the light beam 1400 can be defined based on characteristics such as the angle 1408. In some implementations, the divergence of the light beam 1400 is a beam parameter that can be selected and/or adjusted to facilitate differential coupling. For example, the divergence can affect the extent to which light is (or is not) coupled into one or more linear waveguides.

The light beam 1400 can include coherent light (e.g., a laser beam) which propagates in form of one or more modes. Here, the light beam 1400 has a mode profile 1410 that schematically illustrates (e.g., in terms of intensity and/or spatial distribution) the profile of the at least one mode of the light beam 1400. In some implementations, the mode profile 1410 is a beam parameter that can be selected and/or adjusted to facilitate differential coupling. For example, the mode profile 1410 can affect the extent to which light is (or is not) coupled into one or more linear waveguides.

The light beam 1400 can have one or more polarizations. In some implementations, polarization is a beam parameter that can be selected and/or adjusted to facilitate differential coupling. For example, polarization can affect the extent to which light is (or is not) coupled into one or more linear waveguides.

The light beam 1400 can have any suitable cross-section profile. In some implementations, the light beam 1400 has a rectangular cross-section profile 1412A. For example, one or more dimensions of the rectangular cross-section profile 1412A (e.g., an aspect ratio thereof) is a beam parameter that can be selected and/or adjusted to facilitate differential coupling. In some implementations, the light beam 1400 has a circular cross-section profile 1412B. For example, one or more dimensions of the circular cross-section profile 1412B (e.g., a diameter thereof) is a beam parameter that can be selected and/or adjusted to facilitate differential coupling. The dimension(s) of the rectangular cross-section profile 1412A and/or the circular cross-section profile 1412B can affect the extent to which light is (or is not) coupled into one or more linear waveguides.

The light beam 1400 can include electromagnetic radiation of one or more wavelengths. In some implementations, the wavelength(s) of the light beam 1400 is a beam parameter that can be selected and/or adjusted to facilitate differential coupling. Wavelength(s) can affect the extent to which light is (or is not) coupled into one or more linear waveguides. For example, different wavelengths couple into a grating at different angles. A change in the wavelength and the angle of the light beam 1400 can allow differential coupling.

In some implementations, one or more parameters affecting differential coupling can relate to the grating that couples light into the linear waveguide for the analysis. For example, a coupler (e.g., a grating) may be relatively sensitive to one or more parameters, so a relatively minor change in the parameter(s) can facilitate differential coupling.

Figure 15A:
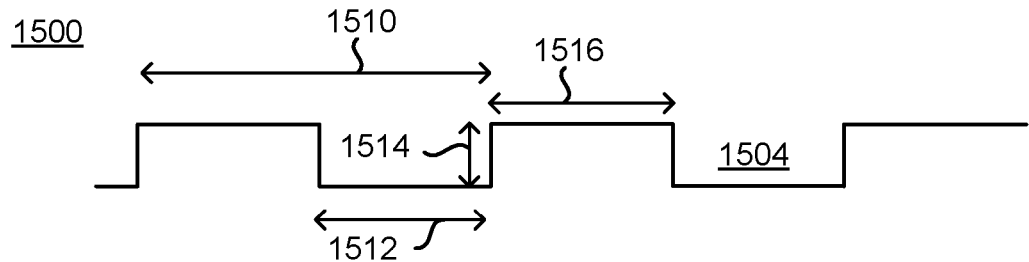
FIGS. 15A-15C show examples of gratings.
Figure 15B:

FIGS. 15A-15B show examples of gratings 1500 and 1502. The grating 1500 and/or 1502 can be used with one or more methods described herein, and/or be used in combination with one or more systems or apparatuses described herein.

The gratings 1500 and 1502 can have the same or different refractive indices from each other. In some implementations, the refractive index is a coupler parameter that can be selected and/or adjusted to facilitate differential coupling. For example, the refractive index can affect the extent to which light is (or is not) coupled into one or more linear waveguides.

The grating 1500 here includes grooves 1504, and the grating 1502 includes grooves 1506 and 1508. At least one groove pitch 1510 can be defined for each of the gratings 1500 and 1502. The groove pitch 1510 can represent the distance from an edge of one of the grooves 1504, 1506 or 1508, to the corresponding edge of the adjacent one of the grooves 1504, 1506 or 1508. In some implementations, the groove pitch 1510 is a coupler parameter that can be selected and/or adjusted to facilitate differential coupling. For example, the groove pitch 1510 can affect the extent to which light is (or is not) coupled into one or more linear waveguides.

At least one groove width 1512 can be defined for each of the grooves 1504, 1506 or 1508. The groove width 1512 can represent the width from edge to edge of one of the grooves 1504, 1506 or 1508. In some implementations, the groove width 1512 is a coupler parameter that can be selected and/or adjusted to facilitate differential coupling. For example, the groove width 1512 can affect the extent to which light is (or is not) coupled into one or more linear waveguides.

At least one groove height 1514 can be defined for each of the grooves 1504, 1506 or 1508. The groove height 1514 can represent the height from the bottom to the opening of one of the grooves 1504, 1506 or 1508. In some implementations, the groove height 1514 is a coupler parameter that can be selected and/or adjusted to facilitate differential coupling. For example, the groove height 1514 can affect the extent to which light is (or is not) coupled into one or more linear waveguides.

At least one groove spacing 1516 can be defined for each of the grooves 1504, 1506 or 1508. The groove spacing 1516 can represent the distance from the edge of one of the grooves 1504, 1506 or 1508 to the nearest edge of the adjacent one of the grooves 1504, 1506 or 1508. In some implementations, the groove spacing 1516 is a coupler parameter that can be selected and/or adjusted to facilitate differential coupling. For example, the groove spacing 1516 can affect the extent to which light is (or is not) coupled into one or more linear waveguides.

In some implementations, a non-uniform grating can be used. In some implementations, the grooves 1506 and 1508 of the grating 1502 provide a non-uniform grating. For example, the grooves 1506 and 1508 may have different groove widths 1512. As another example, the grooves 1506 and 1508 may instead or additionally have different groove pitches 1510, different groove heights 1514, and/or different groove spacing 1516. As such, the grating 1502 is an example of grating non-uniformity.

In some implementations, groove orientation is a coupler parameter that can be selected and/or adjusted to facilitate differential coupling. In some implementations, gratings generally couple in a transverse electric polarization in which the electric field is parallel to the grating grooves. The grating 1500 and/or 1502 can be positioned so as to obtain a particular orientation of the grooves 1504, 1506 and/or 1508. For example, a groove structure can be rotated to another orientation to provide coupling based on a rotated polarization. That is, the groove orientation can affect the extent to which light is (or is not) coupled into one or more linear waveguides.

Figure 15C:
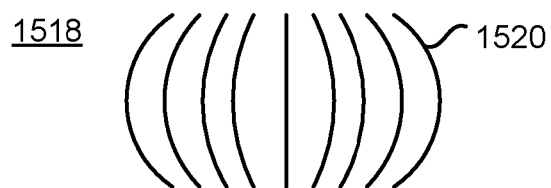

In some implementations, groove curvature is a coupler parameter that can be selected and/or adjusted to facilitate differential coupling. FIG. 15C shows a top view of a grating 1518 with grooves 1520 having different curvatures. For example, the groove curvature can affect the extent to which light is (or is not) coupled into one or more linear waveguides.

Figure 16:
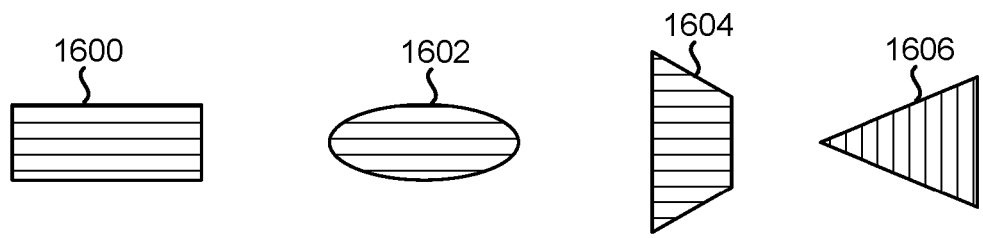
FIG. 16 shows examples of shapes of couplers.

In some implementations, coupler shape is a coupler parameter that can be selected and/or adjusted to facilitate differential coupling. FIG. 16 shows examples of shapes of couplers 1600, 1602, 1604, and 1606. These examples show illustrative shapes of couplers and schematically indicate the grooves of the respective gratings. The coupler 1600 can include a rectangular (e.g., square) grating. For example, the grooves of the grating can be oriented along the longer edge, or the shorter edge, of the rectangle. The coupler 1602 can include an elliptical (e.g., circular) grating. For example, the grooves of the grating can be oriented along the major axis, or along the minor axis, of the grating. The coupler 1604 can include a truncated triangular grating. For example, the grooves of the grating can be oriented perpendicular to the base, or perpendicular to the height, of the triangle. As another example, different angles of the side edges can be used. The coupler 1606 can include a triangular grating. For example, the grooves of the grating can be oriented perpendicular to the base, or perpendicular to the height, of the triangle. As another example, different angles of the side edges can be used. In some implementations, the shape of the coupler(s) can be selected based on (e.g., optimized) the diameter of the illumination beam, or an aspect ratio of the illumination beam, or combinations thereof, to name just a few examples. The coupler shape and/or the orientation of the grooves can affect the extent to which light is (or is not) coupled into one or more linear waveguides.

The shape of the coupler (including, but not limited to, the couplers 1600, 1602, 1604, and 1606) can be selected in view of the diameter, aspect ratio, or other characteristic of the light beam. For example, this can allow the resulting structure to be tuned for a particular differential coupling.

The coupler parameter(s) can be selected and/or adjusted based on a mode profile of the illuminating beam. This can be done by way of selecting (e.g., optimizing) the groove structure. In some implementations, a non-uniform grating can be used. For example, a chirped grating (e.g., a grating with a variation in groove pitch), an apodised grating (e.g., having a refractive index that approaches zero toward an end of the grating), a curved grating, and combinations thereof, can be used. In some implementations, computer-based optimization on one or more coupler parameters (e.g., grating structure) can be performed. For example, this can facilitate differential coupling based on the mode profile of the incident light beam.

In some implementations, one or more parameters affecting differential coupling can relate to the linear waveguide into which light is coupled for the analysis. For example, the coupling may be relatively sensitive to one or more parameters relating to the waveguide, so a relatively minor change in the parameter(s) can facilitate differential coupling.

Figure 17:
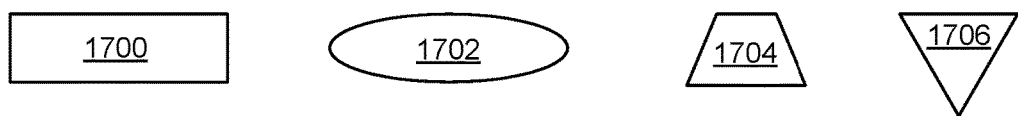
FIG. 17 shows examples of cross-sectional profiles for linear waveguides.

In some implementations, a cross-sectional profile of the linear waveguide is a waveguide parameter that can be selected and/or adjusted to facilitate differential coupling. FIG. 17 shows examples of cross-sectional profiles for linear waveguides. A waveguide 1700 can include a rectangular (e.g., square) profile. For example, a nanowell layer can be positioned adjacent to the longer edge, or the shorter edge, of the rectangle. A waveguide 1702 can include an elliptical (e.g., circular) profile. For example, the nanowell layer can be positioned parallel to the major axis, or parallel to the minor axis, of the waveguide 1702. A waveguide 1704 can include a truncated triangular profile. For example, the nanowell layer can be positioned adjacent to the base, the side edge(s), and/or the truncation face, of the triangle. Different angles of the side edges can be used. A waveguide 1706 can include a triangular profile. For example, the nanowell layer can be positioned adjacent one or more of the sides of the triangle. Different angles of the side edges can be used. The cross-sectional profile can affect the extent to which light is (or is not) coupled into one or more linear waveguides.

In some implementations, the refractive index of the linear waveguide is a waveguide parameter that can be selected and/or adjusted to facilitate differential coupling. For example, the refractive index difference between two or more linear waveguides can affect the extent to which light is (or is not) coupled into the waveguides.

In some implementations, the matching of one or more modes between the linear waveguide and the coupler, or between the linear waveguide and the light beam, or both, is a waveguide parameter that can be selected and/or adjusted to facilitate differential coupling. For example, the dimensions and/or proportions of the linear waveguide can be selected so as to facilitate propagation (or to not facilitate propagation) of a particular mode of incoming light. That is, mode matching with the coupler and/or the light beam can affect the extent to which light is (or is not) coupled into the waveguides.

Examples herein mention that a beam parameter, a coupler parameter, and/or a waveguide parameter can be selected and/or adjusted to facilitate differential coupling. In some implementations, combinations of two or more such parameters can be selected and/or adjusted. For example, the selection/adjustment can take into account at least two beam parameters; or at least one beam parameter and at least one coupler parameter; or at least one beam parameter, at least one coupler parameter, and at least one waveguide parameter. In some implementations, a cross-sectional profile of a waveguide can be used together with a particular grating (e.g., a grating optimized for certain coupling or non-coupling). For example, this can allow the resulting structure to be tuned for different mode profiles, beam diameters, aspect ratios, to name just a few examples.

Figure 18:
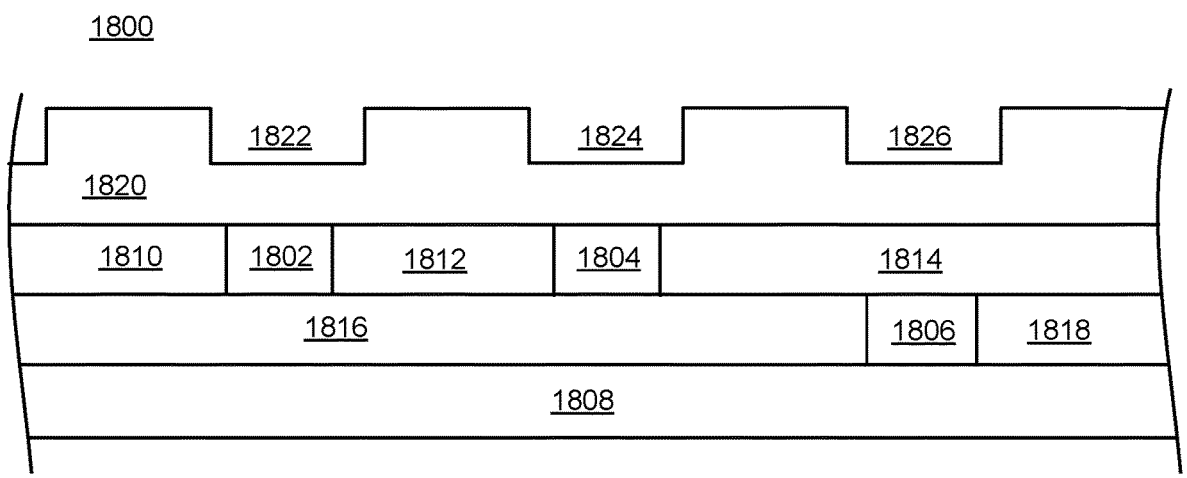
FIG. 18 shows a cross section of part of another example flowcell with linear waveguides.

FIG. 18 shows a cross section of part of another example flowcell 1800 with linear waveguides 1802, 1804 and 1806. The flowcell 1800 can be used with one or more methods described herein, and/or be used in combination with one or more systems or apparatuses described herein. For example, the flowcell 1800 can be used with staggered gratings or non-staggered gratings, or both. As another example, the flowcell 1800 can be used with nanowells arranged in a hexagonal array or a non-hexagonal (e.g., otherwise polygonal) array, or both. Only a portion of the flowcell 1800 is shown, for purposes of illustration. For example, one or more additional layers and/or more or fewer waveguides 1802, 1804 and/or 1806, can be used.

The flowcell 1800 includes a substrate 1808. The substrate 1808 can form a base for the flowcell 1800. In some implementations, one or more other layers can be formed at (e.g., in contact with or near) the substrate 1808 in the manufacturing of the flowcell 1800. The substrate 1808 can serve as a basis for forming the linear waveguides 1802, 1804 and/or 1806. The linear waveguides 1802, 1804 and/or 1806 can initially exist separately from the substrate 1808 and thereafter be applied onto the substrate 1808, or the linear waveguides 1802, 1804 and/or 1806 can be formed by application, and/or removal of, one or more materials to or from the substrate. The linear waveguides 1802, 1804 and/or 1806 can be formed directly onto the substrate 1808, or onto one or more intermediate layers at the substrate 1808.

The linear waveguides 1802, 1804 and/or 1806 serve to conduct electromagnetic radiation (including, but not limited to, visible light, such as laser light). In some implementations, the electromagnetic radiation performs one or more functions during an imaging process. For example, the electromagnetic radiation can serve to excite fluorophores in a sample material for imaging. The linear waveguides 1802, 1804 and/or 1806 can be made of any suitable material that facilitates propagation of one or more kinds of electromagnetic radiation. In some implementations, the material(s) of the linear waveguides 1802, 1804 and/or 1806 can include a polymer material. In some implementations, the material(s) of the linear waveguides 1802, 1804 and/or 1806 can include $Ta_2O_5$ and/or $SiN_x$. For example, the linear waveguides 1802, 1804 and/or 1806 can be formed by sputtering, chemical vapor deposition, atomic layer deposition, spin coating, and/or spray coating.

Each of the linear waveguides 1802, 1804 and/or 1806 can have one or more gratings (omitted here for clarity) to couple electromagnetic radiation into and/or out of that linear waveguide 1802, 1804 and/or 1806. The grating(s) can be positioned in the same layer as the corresponding linear waveguide(s). One or more directions of travel for the electromagnetic radiation in the linear waveguides 1802, 1804 and/or 1806 can be employed. For example, the direction of travel can be into and/or out of the plane of the present illustration. Examples of gratings are described elsewhere herein.

Each of the linear waveguides 1802, 1804 and/or 1806 can be positioned against one or more types of cladding. The cladding can serve to constrain the electromagnetic radiation to the respective linear waveguide 1802, 1804 and/or 1806 and prevent, or reduce the extent of, propagation of the radiation into other linear waveguides 1802, 1804 and/or 1806 or other substrates. Here, claddings 1810, 1812, 1814, 1816, and 1818 are shown as an example. In some implementations, the claddings 1810, 1812, and 1814, together with the linear waveguides 1802 and 1804, can form a first layer in the flowcell 1800. For example, the claddings 1810 and 1812 can be positioned against or near the linear waveguide 1802 on different (e.g., opposing) sides thereof. For example, the claddings 1812 and 1814 can be positioned against or near the linear waveguide 1804 on different (e.g., opposing) sides thereof. In some implementations, the claddings 1816 and 1818, together with the linear waveguide 1806, can form a second layer in the flowcell 1800. For example, the claddings 1816 and 1818 can be positioned against or near the linear waveguide 1806 on different (e.g., opposing) sides thereof. Formation of multiple layers can provide advantages regarding differential coupling. In some implementations, two or more different materials can be used for the respective waveguides. For example, this can facilitate that different refractive indices are given to the respective waveguides and/or couplers. In some implementations, cross-talk between waveguides can be reduced or minimized.

The claddings 1810, 1812, 1814, 1816, and/or 1818 can be made from one or more suitable materials that serve to separate the linear waveguides 1802, 1804 and/or 1806 from each other. In some implementations, the claddings 1810, 1812, 1814, 1816, and/or 1818 can be made from a material having a lower refractive index than the refractive index/indices of the linear waveguides 1802, 1804 and/or 1806. For example, the linear waveguides 1802, 1804 and/or 1806 can have a refractive index of about 1.4-1.6, and the claddings 1810, 1812, 1814, 1816, and/or 1818 can have a refractive index of about 1.2-1.4. In some implementations, one or more of the claddings 1810, 1812, 1814, 1816, and/or 1818 includes a polymer material. In some implementations, one or more of the claddings 1810, 1812, 1814, 1816, and/or 1818 includes multiple structures, including, but not limited to, structures of one material (e.g., polymer) interspersed by regions of vacuum or another material (e.g., air or a liquid).

The flowcell 1800 includes at least one nanowell layer 1820. In some implementations, the nanowell layer 1820 is positioned opposite the first layer from the second layer. For example, the nanowell layer 1820 can be positioned adjacent (e.g., abutting or near) to the linear waveguides 1802 and 1804 and the claddings 1810, 1812, and 1814. The nanowell layer 1820 includes one or more nanowells. In some implementations, the nanowell layer 1820 includes nanowells 1822, 1824, and 1826. The nanowells 1822, 1824, and/or 1826 can be used for holding one or more sample materials during at least part of the analysis process (e.g., for imaging). For example, one or more genetic materials (e.g., in form of clusters) can be placed in the nanowells 1822, 1824, and/or 1826.

The nanowells 1822, 1824, and/or 1826 can be arranged in any pattern, or without a particular pattern, at the nanowell layer 1820. One or more of the nanowells 1822, 1824, and/or 1826 can be at least substantially aligned with one or more of the linear waveguides 1802, 1804 and/or 1806. This can allow interaction between the respective nanowell 1822, 1824, and/or 1826 and the corresponding linear waveguide 1802, 1804 and/or 1806 for imaging purposes (including, but not limited to, by way of transmission of evanescent light). For example, the nanowell 1822 can be at least substantially aligned with the linear waveguide 1802; the nanowell 1824 can be at least substantially aligned with the linear waveguide 1804; and/or the nanowell 1826 can be at least substantially aligned with the linear waveguide 1806. In some implementations, the first layer (e.g., the claddings 1810, 1812, and 1814, together with the linear waveguides 1802 and 1804) can be positioned closer to the nanowell layer 1820 than is the second layer (e.g., the claddings 1816 and 1818, together with the linear waveguide 1806). As another example, the second layer can be positioned further from the third layer than is the first layer.

Figure 19:
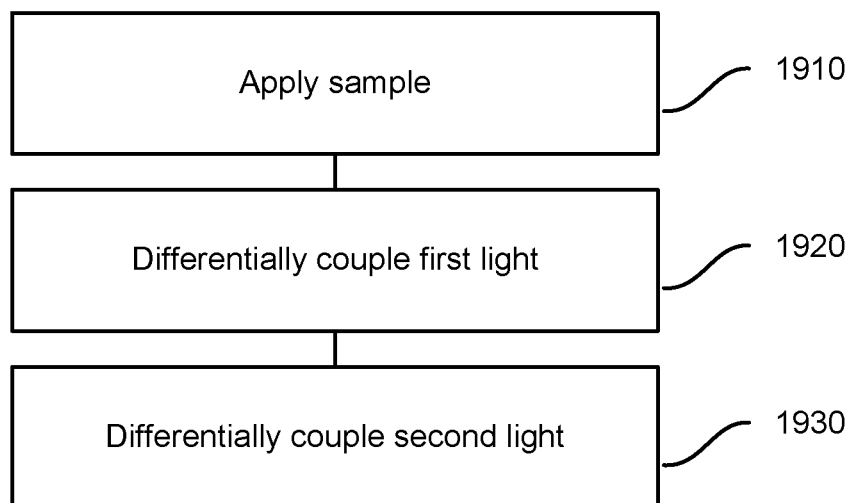
FIG. 19 is a flowchart of an example method.

FIG. 19 is a flowchart of an example method 1900. The method 1900 can be performed using, and/or in combination with, one or more other examples described herein. More or fewer operations can be performed, and/or two or more operations can be performed in a different order, unless otherwise indicated.

At 1910, a sample is applied to at least some nanowells of a flowcell. In some implementations, the sample is applied to a first set of nanowells and a second set of nanowells.

At 1920, first light can be differentially coupled into at least a first linear waveguide associated with the first set of nanowells. In some implementations, the first light can be differentially coupled using a first grating.

At 1930, second light can be differentially coupled into at least a second linear waveguide associated with the second set of nanowells. In some implementations, the second light can be differentially coupled using a second grating.

The terms "substantially" and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. Also, when used herein, an indefinite article such as "a" or "an" means "at least one."

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

A number of implementations have been described. Nevertheless, it will be understood that various modifications may be made without departing from the spirit and scope of the specification.

In addition, the logic flows depicted in the figures do not require the particular order shown, or sequential order, to achieve desirable results. In addition, other processes may be provided, or processes may be eliminated, from the described flows, and other components may be added to, or removed from, the described systems. Accordingly, other implementations are within the scope of the following claims.

While certain features of the described implementations have been illustrated as described herein, many modifications, substitutions, changes and equivalents will now occur to those skilled in the art. It is, therefore, to be understood that appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. A flowcell comprising:
    a substrate;
    a nanowell layer having a first set of nanowells and a second set of nanowells to receive a sample;
    a first linear waveguide associated with the first set of nanowells;
    a second linear waveguide associated with the second set of nanowells;
    a first grating for the first linear waveguide; and
    a second grating for the second linear waveguide, the first linear waveguide and the second linear waveguide positioned between a portion of the substrate and the nanowell layer,
    wherein one or more of the first linear waveguide and the second linear waveguide have a waveguide parameter and wherein one or more of the first grating and the second grating have a coupler parameter, the waveguide parameter, the coupler parameter, or both the waveguide parameter and the coupler parameter providing differential coupling of light into the first linear waveguide and the second linear waveguide.

2. The flowcell of claim 1, wherein the waveguide parameter comprises at least one of: a cross sectional profile, a refractive index difference, a mode matching, or combinations thereof.

3. The flowcell of claim 1, wherein the coupler parameter comprises at least one of: a refractive index, a pitch, a groove width, a groove height, a groove spacing, a grating non-uniformity, a groove orientation, a groove curvature, a coupler shape, or combinations thereof.

4. The flowcell of claim 1, wherein at least one of the first grating or the second grating is formed by at least one of slits, grooves, ridges, bands, or protruding longitudinal structures.

5. The flowcell of claim 1, further comprising first cladding on either side of the first grating and second cladding on either side of the second grating.

6. The flowcell of claim 1, wherein the first linear waveguide and the second linear waveguide are formed directly on the substrate.

7. The flowcell of claim 1, further comprising an intermediate layer and wherein the first linear waveguide and the second linear waveguide are formed on the intermediate layer, wherein the intermediate layer is positioned between the substrate and the first linear waveguide and the second linear waveguide.

8. The flowcell of claim 1, wherein the first grating and the second grating are staggered.

9. The flowcell of claim 1, wherein the first set of nanowells comprises a first row of nanowells that is aligned with the first linear waveguide and the second set of nanowells comprises a second row of nanowells that is aligned with the second linear waveguide.

10. The flowcell of claim 1, wherein the first set of nanowells comprises a first polygonal array of nanowells and the second set of nanowells comprises a second polygonal array of nanowells.

11. The flowcell of claim 1, wherein the first grating is spatially offset from the second grating in a direction that is substantially parallel to the first linear waveguide and the second linear waveguide.

12. The flowcell of claim 1, wherein the first grating is to couple first light to the first linear waveguide without coupling the first light to the second linear waveguide.

13. The flowcell of claim 1, further comprising a light area aligned with the first grating but not aligned with the second grating.

14. The flowcell of claim 1, wherein the first grating and the second grating have different grating periods from each other.

15. The flowcell of claim 1, wherein the first grating has a first refractive index and the second grating has a second refractive index.

* * * * *